United States Patent [19]

Harrison et al.

[11] Patent Number: 5,620,989
[45] Date of Patent: Apr. 15, 1997

[54] 4-ARYLMETHYLOXYMETHYL PIPERIDINES AS TACHYKININ ANTAGONSITS

[75] Inventors: Timothy Harrison, Great Dunmow; Angus M. MacLeod, Bishops Stortford; Graeme I. Stevenson, Saffron Walden; Brian J. Williams, Great Dunmow, all of United Kingdom

[73] Assignee: Merck Sharp & Dohme Limited, Hoddesdon, England

[21] Appl. No.: 416,813

[22] PCT Filed: Oct. 27, 1993

[86] PCT No.: PCT/GB93/02214

§ 371 Date: Apr. 13, 1995

§ 102(e) Date: Apr. 13, 1995

[87] PCT Pub. No.: WO94/10165

PCT Pub. Date: May 11, 1994

[30] Foreign Application Priority Data

| Oct. 28, 1992 | [GB] | United Kingdom | 9222633 |
| Apr. 30, 1993 | [GB] | United Kingdom | 9308962 |
| Jul. 2, 1993 | [GB] | United Kingdom | 9313680 |
| Aug. 4, 1993 | [GB] | United Kingdom | 9316112 |

[51] Int. Cl.$^6$ ................ C07D 401/06; C07D 417/06; C07D 211/10; A61K 31/445; A61K 31/47

[52] U.S. Cl. ................ 514/317; 514/314; 514/328; 546/192; 546/193; 546/176

[58] Field of Search ................ 546/192, 193, 546/176; 519/317; 514/314, 318

[56] References Cited

FOREIGN PATENT DOCUMENTS 0337167 10/1989 European Pat. Off. .
0522808A2 1/1993 European Pat. Off. .

*Primary Examiner*—David B. Springer
*Attorney, Agent, or Firm*—J. Eric Thies; David L. Rose

[57] ABSTRACT

The present invention is directed to compounds of the formula (I)

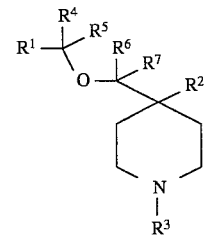

wherein $R^1$, $R^2$, $R^3$, $R^4$, $R^5$, $R^6$, and $R^7$ are defined herein, and pharmaceutically acceptable salts thereof, which are useful as tachykinin antagonists,

12 Claims, No Drawings

4-ARYLMETHYLOXYMETHYL PIPERIDINES AS TACHYKININ ANTAGONSITS

This application is A371 of PCT/GB93/02214 filed Oct. 27, 1993.

This invention relates to a class of azacyclic compounds, which are useful as tachykinin antagonists. More particularly, the compounds of the invention comprise an azacyclic ring system substituted by an arylmethyloxy or arylmethylthio moiety.

The tachykinins are a group of naturally-occurring peptides found widely distributed throughout mammalian tissues, both within the central nervous system and in the peripheral nervous and circulatory systems. The structures of three known mammalian tachykinins are as follows:

Substance P:
  Arg-Pro-Lys-Pro-Gln-Gln-Phe-Phe-Gly-Leu-Met-NH$_2$
Neurokinin A:
  His-Lys-Thr-Asp-Ser-Phe-Val-Gly-Leu-Met-NH$_2$
Neurokinin B:
  Asp-Met-His-Asp-Phe-Phe-Val-Gly-Leu-Met-NH$_2$ Evidence for the usefulness of tachykinin receptor antagonists in pain, headache, especially migraine, Alzheimer's disease, multiple sclerosis, attenuation of morphine withdrawal, cardivascular changes, oedema, such-as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero and A. Giachetti, J. Auton. Pharmacol. (1993) 13, 23–93. Tachykinin antagonists are also believed to be useful in allergic conditions [Hamelet et. al Can. J. Pharmacol. Physiol. (1988) 66 1361–7], immunoregulation [Lotz et al Science (1988) 241 1218–21 and Kimball et al, J. Immunol. (1988) 141 (10) 3564–9], and as anticonvulsants [Garant et al., Brain Research (1986) 382 372–8]. Tachykinin antagonists may also be useful in the treatment of small cell carcinomas, in particular small cell lung cancer (SCLC) [Langdon et al., Cancer Research (1992) 52, 4554–7].

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosis (European patent application no. 0 436 334), conjuctivitis, vernal conjunctivitis, contact dermatitis, atropic dermatitis, urticaria, and other eczematoid dermatitis (European patent application no. 0 394 989) and emesis (European patent application no. 0 533 280).

In view of their metabolic instability, peptide derivatives are likely to be of limited utility as therapeutic agents. It is for this reason that non-peptide tachykinin antagonists are sought.

In essence, this invention provides a class of potent non-peptide tachykinin antagonists.

The present invention provides a compound of formula (I), or a salt or prodrug thereof:

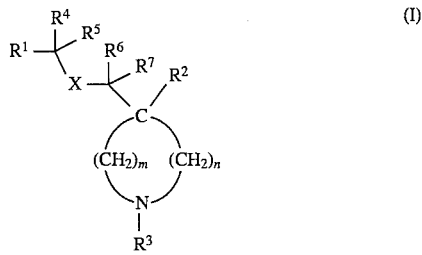

wherein
m is 2, 3 or 4;
n is 0, 1 or 2 when m is 2 or 3, and n is 0 or 1 when m is 4;
X represents O or S;
$R^1$ represents phenyl optionally substituted by 1, 2 or 3 groups selected from $C_{1-6}$alkyl, $C_{2-6}$ alkenyl, $C_{2-6}$ alkynyl, halo, cyano, nitro, trifluoromethyl, trimethylsilyl, —OR$^a$, SR$^a$, SOR$^a$, SO$_2$R$^a$, —NR$^a$R$^b$, —NR$^a$COR$^b$, —NR$^a$CO$_2$R$^b$, —CO$_2$R$^a$ or —CONR$^a$R$^b$, where $R^a$ and $R^b$ each independently represent H, $C_{1-6}$alkyl, phenyl or trifluoromethyl;
$R^2$ represents phenyl optionally substituted by 1, 2 or 3 groups selected from $C_{1-6}$alkyl, $C_{2-6}$ alkenyl, $C_{2-6}$ alkynyl, halo, cyano, nitro, trifluoromethyl, trimethylsilyl, —OR$^a$, SR$^a$, SOR$^a$, SO$_2$R$^a$, —NR$^a$R$^b$, —NR$^a$COR$^b$, —NR$^a$CO$_2$R$^b$, —CO$_2$R$^a$ or —CONR$^a$R$^b$, where $R^a$ and $R^b$ are as previously defined; heteroaryl selected from indazolyl, thienyl, furyl, pyridyl, thiazolyl, tetrazolyl and quinolyl; benzhydryl; or benzyl; wherein each heteroaryl and each phenyl moiety of benzyl and benzhydryl may be substituted by $C_{1-6}$alkyl, $C_{1-6}$alkoxy, halo or trifluoromethyl; and
$R^3$ represents H, COR$^9$, CO$_2$R$^{10}$, COCONR$^{10}$R$^{11}$, COCO$_2$R$^{10}$, SO$_2$R$^{15}$, CONR$^{10}$SO$_2$R$^{15}$, $C_{1-6}$alkyl optionally substituted by a group selected from (CO$_2$R$^{10}$, CONR$^{10}$R$^{11}$, hydroxy, cyano, COR$^9$, NR$^{10}$R$^{11}$, C(NOH)NR$^{10}$R$^{11}$, CONHphenyl($C_{1-4}$alkyl), COCO$_2$R$^{10}$, COCONR$^{10}$R$^{11}$, SO$_2$R$^{15}$, CONR$^{10}$SO$_2$R$^{15}$ and phenyl optionally substituted by one or more substituents selected from $C_{1-6}$alkyl, $C_{1-6}$alkoxy, halo and trifluoromethyl), Y—R$^8$ or CO—Z—(CH$_2$)$_q$—R$^{12}$;
$R^4$, $R^5$, $R^6$ and $R^7$ each independently represent H or $C_{1-6}$alkyl;
$R^8$ represents an optionally substituted aromatic heterocycle;
$R^9$ represents H, $C_{1-6}$alkyl or phenyl;
$R^{10}$ and $R^{11}$ each independently represent H or $C_{1-6}$alkyl;
$R^{12}$ represents NR$^{13}$R$^{14}$ or an optionally substituted aromatic or non-aromatic azacyclic or azabicyclic group;
$R^{13}$ and $R^{14}$ each independently represent H, $C_{1-6}$alkyl, phenyl optionally substituted by one or more of $C_{1-6}$alkyl, $C_{1-6}$alkoxy, halo or trifluoromethyl or phenyl$C_{1-4}$alkyl optionally substituted in the phenyl ring by one or more of $C_{1-6}$alkyl, $C_{1-6}$alkoxy, halo or trifluoromethyl;
$R^{15}$ represents $C_{1-6}$alkyl, trifluoromethyl or phenyl optionally substituted by one or more substituents selected from $C_{1-6}$alkyl, $C_{1-6}$alkoxy, halo and trifluoromethyl;
Y represents a hydrocarbon chain of 1,2,3 or 4 carbon atoms which may optionally be substituted by oxo;

Z represents $CH_2$, O, S or $NR^{10}$; and q represents 0, 1, 2, 3, 4, 5 or 6.

As used herein, the definition of each expression, when it occurs more than once in any structure, is intended to be independent of its definition elsewhere in the same structure.

The alkyl, alkenyl and alkynyl groups referred to with respect to the formulae herein may represent straight, branched or cyclic groups, or combinations thereof. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkyl-alkyl groups such as cyclopropylmethyl; suitable alkenyl groups include vinyl and allyl; and suitable alkynyl groups include propargyl.

The term "halo" as used herein includes fluoro, chloro, bromo and iodo, especially chloro and fluoro.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985. However, most aptly the present invention provides a compound of formula (I) or a pharmaceutically acceptable salt thereof.

Those compounds according to the invention which contain one or more chiral centres may exist both as enantiomers and as diastereomers. It is to be understood that all such isomers and mixtures thereof are encompassed within the scope of the present invention.

Preferably m is 2.

When m is 2, n is preferably 2. When m is 3 or 4, n is preferably 0.

Preferably X represents O.

Preferably $R^1$ represents substituted phenyl. When $R^1$ is substituted phenyl suitable substituents include nitro, trifluoromethyl, trimethylsilyl, bromo, chloro, fluoro, iodo, cyano, methyl, ethyl, cyclopropyl, t-butyl, vinyl, methoxy, phenoxy, amino and carbonylmethoxy. Preferably $R^1$ represents phenyl substituted by one or more groups selected from $C_{1-6}$alkyl such as methyl and t-butyl, halo such as chloro, fluoro and bromo, and trifluoromethyl.

Preferably $R^1$ represents disubstituted phenyl, in particular 3,5-disubstituted phenyl, for example 3,5-disubstituted phenyl wherein the substituents are selected from $C_{1-6}$alkyl, halo and trifluoromethyl. More preferably $R^1$ represents 3,5-bis(trifluoromethyl) phenyl.

Suitable values for the group $R^2$ include unsubstituted or substituted phenyl, 5-membered heteroaryl such as thienyl, 6-membered heteroaryl such as pyridyl, and benzhydryl.

Preferably $R^2$ represents unsubstituted or substituted phenyl.

When $R^2$ represents substituted phenyl a preferred substituent is halo, especially fluoro.

When $R^8$ represents a substituted aromatic heterocycle, suitable substituents in the heterocyclic ring include one or more of $C_{1-6}$alkyl, $C_{1-6}$alkoxy, phenyl, oxo, thioxo, halo, trifluoromethyl, $NR^aR^b$, $NR^aCOR^b$, $CONR^aR^b$, $CO_2R^a$, $SR^a$, $SO_2R^a$ and $CH_2OR^a$, where $R^a$ and $R^b$ are as previously defined. Particular examples of suitable substituents include methyl, methoxy, phenyl, oxo, thioxo, bromo, iodo, $NH_2$, $SCH_3$, $CONH_2$ and cyano. Particularly preferred substituents include oxo and $NH_2$.

Suitable values for $R^8$ include thienyl, furyl, pyrrolyl, pyridyl, pyrazolyl, triazolyl, tetrazolyl, thiazolyl, pyrazinyl, pyrimidinyl, pyridazinyl, triazinyl, oxazolyl, oxadiazolyl, thiadiazolyl, isoxazolyl, quinolyl, isothiazolyl, imidazolyl, benzimidazolyl, benzoxazolyl, benzothiophenyl, benzofuranyl and indolyl, any of which may be substituted.

Preferably $R^8$ represents a substituted or unsubstituted 5- or 6-membered nitrogen containing aromatic heterocycle such as for example oxazolyl, oxadiazolyl, tetrazolyl, thiazolyl, thiadiazolyl, triazolyl, pyrazinyl, pyridyl, pyrimidinyl, pyridazinyl, imidazolyl or triazinyl. More preferably $R^8$ represents optionally substituted oxazolyl, oxadiazolyl, imidazolyl, thiadiazolyl, triazolyl, pyrazinyl, pyrimidinyl, pyridazinyl or triazinyl, or tetrazolyl substituted by $C_{1-6}$alkyl, preferably methyl.

It will be appreciated that, when the heterocyclic moiety $R^8$ is substituted by an oxo or thioxo substituent, different tautomeric forms are possible so that the substituent may be represented as =O or —OH, or =S or —SH, respectively. For the avoidance of doubt, all such tautomeric forms are embraced by the present invention. Favoured heterocyclic moieties $R^8$ include 5 membered heterocyclic rings containing 1, 2 or 3 nitrogen atoms substituted by oxo. A particularly favoured such moiety is 1,2,4-triazol-3-one.

When $R^{12}$ represents $NR^{13}R^{14}$, $R^{13}$ and $R^{14}$ are preferably both $C_{1-6}$alkyl such as methyl, ethyl, n-propyl, i-propyl, n-butyl, i-butyl or t-butyl. More preferably $R^{13}$ and $R^{14}$ will both represent methyl.

When $R^{12}$ represents an aromatic or non-aromatic azacycle or azabicycle it may contain one or more additional heteroatoms selected from O, S and N or groups $NR^{16}$, where $R^{16}$ is H, $C_{1-6}$alkyl or phenyl$C_{1-4}$alkyl, and may be unsubstituted or substituted. Suitable substituents include $C_{1-6}$alkyl, $C_{1-6}$alkoxy, oxo, SH, =S, halo, trifluoromethyl $NR^aR^b$, $NR^aCOR^b$, $CONR^aR^b$, $CO_2R^a$ and $CH_2OR^a$, where $R^a$ and $R^b$ are as previously defined.

When $R^{12}$ represents an aromatic azacycle or azabicycle, suitable values of $R^{12}$ include imidazolyl, triazolyl, tetrazolyl, oxazolyl, thiazolyl, pyrrolyl, pyrazolyl, pyrazinyl, pyridyl, oxadiazolyl, thiadiazolyl, isoxazolyl, isothiazolyl, benzimidazolyl, benzoxazolyl and indolyl, preferably imidazolyl, such as 2,4-imidazolyl, or pyridyl, more preferably pyridyl such as 4-, 3- or 2-pyridyl.

When $R^{12}$ represents a non-aromatic azacycle or azabicycle, suitable values of $R^{12}$ include morpholinyl, piperdinyl, pyrrolidinyl, piperazinyl, methylpiperazinyl, azanorbornanyl, azabicyclo[2.2.2]octanyl and azabicyclo[3.2.2]nonyl, preferably morpholinyl, methylpiperazinyl, quinuclidinyl (azabicyclo[2.2.2]octanyl) or azabicyclo[3.2.2]nonyl, more preferably quinuclidinyl.

Suitably Y represents a hydrocarbon chain of 1 or 2 carbon atoms optionally substituted by oxo, such as $CH_2$, C=O, $CH(CH_3)$, $CH_2(C=O)$ or $(C=O)CH_2$. Preferably Y represents $CH_2$, $CH(CH_3)$ or $CH_2(C=O)$, more preferably $CH_2$ or $CH(CH_3)$.

Suitably q represents 0, 1, 2 or 3.

Suitable values of $R^3$ include H, $COR^9$ such as $COCH_3$, $SO_2R^{15}$ such as $SO_2CH_3$, $C_{1-6}$alkyl such as $CH_3$, $CH(CH_3)_2$, $CH_2CH(CH_3)_2$ and $CH_2CH_2C(CH_3)_3$, $C_{1-6}$alkyl substituted by $CO_2R^{10}$ such as $CH_2CO_2CH_3$, $CH_2CO_2H$, $(CH_2)_3CO_2CH_3$ and $(CH_2)_3CO_2H$, $C_{1-6}$alkyl substituted by $CONR^{10}SO_2R^{15}$ such as $CH_2CONHSO_2CH_3$ and $CH_2CONHSO_2C_6H_5$, $C_{1-6}$alkyl substituted by phenyl, Y—$R^8$ and CO—Z—$(CH_2)_q$—$R^{12}$. Aptly $R^4$, $R^5$, R and $R^7$ independently represent H or methyl. More aptly $R^4$, $R^5$ and $R^6$ represent H.

In one preferred subgroup of compounds according to the invention, $R^3$ represents H or $C_{1-6}$alkyl, more preferably H.

In a further preferred subgroup of compounds according to the invention $R^3$ represents Y—$R^8$.

A yet further preferred subgroup of compounds according to the invention is represented by compounds wherein $R^3$ is $CO-Z-(CH_2)_q-R^{12}$.

A particular sub-class of compounds according to the invention is represented by compounds of formula (Ia), and salts and prodrugs thereof:

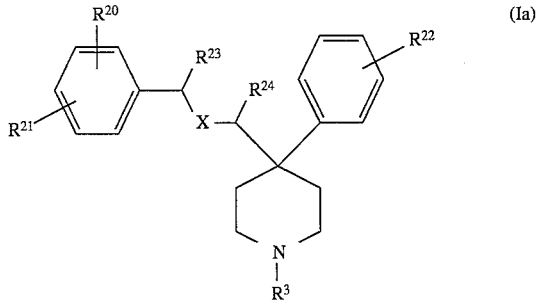

wherein $R^3$ and X are as defined for formula (I);

$R^{20}$ and $R^{21}$ independently represent H, $C_{1-6}$alkyl, $C_{2-6}$alkenyl, $C_{2-6}$alkynyl, halo, cyano, nitro, trifluoromethyl trimethylsilyl $OR^a$, $SR^a$, $SOR^a$, $SO_2R^a$, $NR^aR^b$, $NR^aCOR^b$, $NR^aCO_2R^b$, $COR^a$ or $CONR^aR^b$, where $R^a$ and $R^b$ are as previously defined;

$R^{22}$ represents H or halo, preferably H or fluoro, for example 4-fluoro; and $R^{23}$ and $R^{24}$ each independently represent H or methyl. Aptly $R^{24}$ represents H. Aptly $R^{23}$ represents methyl.

Particular values of $R^{20}$ and $R^{21}$ include H, chloro, bromo, methyl, t-butyl and trifluoromethyl; and also $C_{1-6}$ alkoxyl groups such as methoxyl, ethoxyl and isopropoxyl and n, sec- and tert-butoxyl. Preferably $R^{20}$ and $R^{21}$ are both other than H and are located at the 3- and 5-positions of the phenyl ring.

A further sub-class of compounds according to the invention is represented by compounds of formula (Ib), and salts and prodrugs thereof:

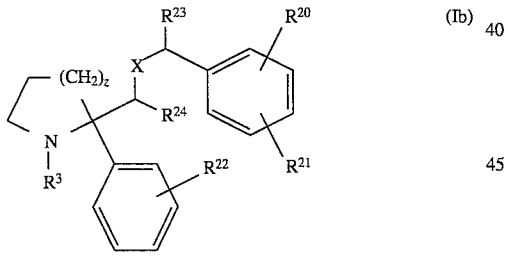

wherein $R^3$, X, $R^{20}$, $R^{21}$, $R^{22}$, $R^{23}$ and $R^{24}$ are as defined for formula (Ia), above and z is 1 or 2.

Specific compounds within the scope of the present invention include:

4-phenyl-4-[(3,5-bistrifluoromethyl)benzyloxy methyl]piperidine;

2-[(3,5-bistrifluoromethyl)benzyloymethyl]-2-phenylpyrrolidine;

4-phenyl-4-[(2-trifluoromethyl)benzyloxymethyl]piperidine;

4-phenyl-4-benzyloxymethylpiperidine;

4-phenyl-4-[(3-chloro-5-t-butyl)benzyloxymethyl]piperidine;

4-phenyl-4-[(3,5-dichloro)benzyloxymethyl]piperidine;

4-phenyl-4-[(3-trifluoromethyl)benzyloxymethyl]piperidine;

4-phenyl-4-[(4-trifluoromethyl)benzyloxymethyl]piperidine;

1-acetyl-4-phenyl-4-[(3,5-bistrifluoromethyl)benzyloxymethyl]piperidine;

1-methanesulphonyl-4-phenyl-4-[(3,5-bistrifluoromethyl)benzyloxymethyl]piperidine;

5-[(4-[(3,5-bistrifluoromethyl)benzyloxymethyl]-4-phenylpiperidin-1-ylmethyl]-2,4-dihydro[1,2,4]triazol-3-one;

2-[1'-imidazolyl]acetyl-4-phenyl-4-[(3,5-bistrifluoromethyl)benzyloxymethyl]piperidine;

5-[4-[(3,5-bistrifluoromethyl)benzyloxymethyl]-4-(4-fluorophenyl)-piperidin-1-ylmethyl]-2,4-dihydro[1,2,4]triazol-3-one;

5-[4-[(3,5-bistrifluoromethyl)benzyloxymethyl]-4-(2-fluorophenyl)-piperidin-1-yl)methyl]-2,4-dihydro[1,2,4]triazol-3-one;

5-[4-[(3,5-bistrifluoromethyl)benzyloxymethyl]-4-(3-fluorophenyl)-piperidin-1-yl)methyl]-2,4-dihydro[1,2,4]triazol-3-one;

3-phenyl-3-[(3,5-bistrifluoromethyl)benzyloxymethyl]piperidine);

4-phenyl-[4-[1-(3,5-bis(trifluoromethyl)phenyl]ethoxymethyl]piperidine;

1-methyl-4-phenyl-4-[3,5-bis(trifluoromethyl)benzyloxymethyl]piperidine;

1-isopropyl-4-phenyl-4-[3,5-bis(trifluoromethyl)benzyloxymethyl]piperidine;

1-(2-phenyl)ethyl-4-phenyl-4-[3,5-bis(trifluoromethyl)benzyloxymethyl]piperidine;

1-isobutyryl-4-phenyl-4-[3,5-bis(trifluoromethyl)benzyloxymethyl]piperidine;

1-isovaleryl-4-phenyl-4-[3,5-bis(trifluoromethyl)benzyloxymethyl]piperidine;

(±)-5-[4-[1-(3,5-bis(trifluoromethyl)phenyl]ethoxymethyl]-4-phenyl-piperidin-1-yl]-2,4-dihydro[1,2,4]triazol-3-one;

4-phenyl-4-[(3-chloro-5-methyl)benzyloxymethyl]piperidine;

4-phenyl-4-[(3-bromo-5-methyl)benzyloxymethyl]piperidine;

4-phenyl-4-[(3-methyl-5-t-butyl)benzyloxymethyl]piperidine;

methyl-2-[4-phenyl-4-(3,5-bis(trifluoromethyl)benzyloxymethyl)piperidine]acetate;

N-methyl-4-phenyl-4-[3,5-bis(trifluoromethyl)benzyloxymethyl]piperidine;

4-[3,5-bis(trifluoromethyl)benzyloxymethyl]-4-phenyl-1-(4H-[1,2,4]triazol-3-yl-methyl)piperidine;

5-[4-(3-methyl-5-t-butyl)benzyloxymethyl)4-phenylpiperidin-1-ylmethyl]2,4-dihydro-[1,2,4]triazol-3-one;

2-[4-phenyl-4-[3,5-bis(trifluoromethyl)benzyloxymethyl]-N-3-pyridylmethyl-N-methylacetamide;

4-[3,5-bis(trifluoromethyl)benzyloxymethyl]-1-(2-methylthiazol-5-ylmethyl)-4-phenylpiperidine;

4-[3,5-bis(trifluoromethyl)benzyloxymethyl]-1-[1,2,4]oxadiazol-3-ylmethyl-4-phenylpiperidine;

(±)-5-[4-(3,5-bis(trifluoromethyl)benzyloxymethyl)-4-phenylpiperidinyl-1-ethyl]-2,4-dihydro-[1,2,4]triazol-3-one;

1-[4-(3,5-bis(trifluoromethyl)benzyloxymethyl-4-phenylpiperidin-1-yl]-2-pyrrolidin-1-ylacetamide;

N-methanesulphonyl-2-[4-phenyl-4-(3,5-bis(trifluoromethyl)benzyloxymethyl)piperidin-1-yl]acetamide;

N-phenylsulphonyl-2-[4-phenyl-4-(3,5-bis(trifluoromethyl)benzyloxymethyl)piperidin-1-yl]acetamide;

4-phenyl-4-[(3-phenyl)benzyloxymethyl]piperidine;

5-[4-(3-phenyl)benzyloxymethyl]-4-phenylpiperidin-1-ylmethyl]-2,4-dihydro-[1,2,4]triazol-3-one;

5-[(4-benzyloxymethyl)-4-phenyl-piperidin-1-ylmethyl]-2,4-dihydro-[1,2,4]triazol-3-one;

N-[2-amino-2-methylpropionamido]-4-phenyl-4-[3,5-bis(trifluoromethyl)benzyloxymethyl]piperidine;

4-phenyl-4-[3,5-bis(trifluoromethyl)benzyloxyethyl]piperidine;

4-(3,4-dichlorophenyl)-4-[3,5-bis(trifluoromethyl)benzyloxymethyl]piperidine;

1-[4-(3,5-bis(trifluoromethyl)benzyloxymethyl)-4-phenylpiperidin-1-yl]-2-pyridin-3-ylethanone;

1-[4-(3,5-bis(trifluoromethyl)benzyloxymethyl)-4-phenylpiperidin-1-yl]-2-pyridin-2-ylethanone;

1-[4-(3,5-bis(trifluoromethyl)benzyloxymethyl)-4-phenylpiperidin-1-yl]-2-pyridin-4-ylethanone;

1-[4-(3,5-bis(trifluoromethyl)benzyloxymethyl)-4-phenylpiperidin-1-yl]-3-dimethylamino-propan-1-one;

2-[4-(3,5-bis(trifluoromethyl)benzyloxymethyl)-4-phenylpiperidin-1-yl]acetate;

4-[4-(3,5-bis(trifluoromethyl)benzyloxymethyl)-4-phenylpiperidin-1-yl]butyrate;

methyl-4-[4-(3,5-bis(trifluoromethyl)benzyloxymethyl)-4-phenyl-piperidin-1-yl]butyrate;

1-[4-(3,5-bis(trifluoromethyl)benzyloxymethyl)-4-phenylpiperidin-1-yl]-3-dimethylaminoethanone;

1-[4-(3,5-bis(trifluoromethyl)benzyloxymethyl)-4-phenylpiperidin-1-yl]-3-dimethylaminopent-1-one;

4-(3,5-bis(trifluoromethyl)benzyloxymethyl)-1-[1-(4-toluenesulphonyl)-imidazole-2-yl]methyl-4-phenylpiperidine;

4-(3,5-bis(trifluoromethyl)benzyloxymethyl)-1-(1H-imidazole-2-yl-methyl)-4-phenyl-piperidine;

5-[4-(1-[3-bromophenyl]-ethoxymethyl)-4-phenyl-piperidin-1-ylmethyl]-2,4-dihydro-[1,2,4]-triazol-3-one;

4-phenyl-4-(1-(3-bromophenyl)-ethoxymethyl)-piperidine hydrochloride;

5-[4-(1-[3-chlorophenyl]-ethoxymethyl)-4-phenyl-piperidin-1-ylmethyl]-2,4-dihydro-[1,2,4]-triazol-3-one;

4-phenyl-4-[3-iodobenzyloxymethyl]-ethoxymethyl)piperidine;

5-[4-(3-iodobenzyloxymethyl)-4-phenyl-piperidin-1-ylmethyl]-2,4-dihydro-[1,2,4]-triazol-3-one;

4-phenyl-4-[3-chlorobenzyloxymethyl]-piperidine hydrochloride;

5-[4-(3-chlorobenzyloxymethyl)-4-phenyl-piperidin-1-ylmethyl]-2,4-dihydro-[1,2,4]-triazol-3-one;

1-[4-(3,5-dimethoxybenzyloxymethyl)-4-phenyl-piperidin-1-yl]-2-(1H-indole-3-yl) acetamide;

4-[4-(3,5-dimethoxybenzyloxymethyl)-4-phenyl-piperidin-1-ylmethyl]-quinoline;

3-[2-[4-(3,5-dimethoxybenzyloxymethyl)-4-phenylpiperidin-1-yl]ethyl]-1H-indole;

1-(4-[3,5-dichlorophenyl]-ethoxymethyl)-4-phenylpiperidin-1-yl)-2-pyrrolidin-acetamide hydrochloride;

4-phenyl-4-[3-t-butylbenzyloxymethyl]-piperidine;

4-phenyl-4-[3-cyanobenzyloxymethyl]-piperidine;

5-[4-(3-cyanobenzyloxymethyl)-4-phenyl-piperidin-1-ylmethyl]-2,4-dihydro-[1,2,4]-triazol-3-one;

4-phenyl-4-[4-cyanobenzyloxymethyl]-piperidine hydrochloride;

5-[4-(4-cyanobenzyloxymethyl)-4-phenyl-piperidin-1-ylmethyl]-2,4-dihydro-[1,2,4]-triazol-3-one;

5-[4-(3-t-butylbenzyloxymethyl)-4-phenyl-piperidin-1-ylmethyl]-2,4-dihydro-[1,2,4]-triazol-3-one;

1-[4-(3,5-dimethoxybenzyloxymethyl)-4-phenyl-piperidin-1-yl]-3-piperidin-4-yl-propionamide hydrochloride;

1-(4-(3,5-dichlorobenzyloxymethyl)-4-phenyl-piperidin-1-yl]-2-pyrrolidine acetamide hydrochloride;

4-[3-chloro-5-methoxybenzyloxymethyl)-4-phenyl-piperidine hydrochloride;

5-[4-(3-chloro-5-methoxybenzyloxymethyl)-4-phenylpiperidin-1-ylmethyl]-2,4-dihydro-[1,2,4]-triazol-3-one;

4-[3,5-bis(trifluoromethyl)benzyloxymethyl]-4-phenyl-1-(5-pyrrollodineethyl)carbamate piperidine hydrochloride;

5-[4-(3,5-bismethylbenzyloxymethyl)-4-phenyl-piperidin-1-ylmethyl]-2,4-dihydro-[1,2,4]-triazol-3-one;

(±)-5-[4-(1-(3-N,N-dimethylphenyl)-ethoxymethyl)-4-phenyl-piperidin-1-ylmethyl]-2,4-dihydro-[1,2,4]-triazol-3-one;

4-phenyl-4-[1-(3-isopropoxy)benzyloxymethyl]piperidine hydrochloride;

5-[4-(1-(3-isopropoxyphenyl)-ethoxymethyl)-4-phenylpiperidin-1-ylmethyl]-2,4-dihydro-[1,2,4]-triazol-3-one;

-phenyl-4-(2-cyanobenzyloxymethyl)piperidine hydrochloride;

4-(4-methoxyphenyl)-4-[(3,5-bis(trifluoromethyl)benzyloxymethyl]piperidine hydrochloride;

4-phenyl-4-[(2-methoxy-5-bromo)benzyloxymethyl]piperidine hydrochloride;

4-phenyl-4-[1-(3,6-dichlorophenyl)ethoxymethyl]piperidine hydrochloride;

4-phenyl-4-[1-(2,3-dichlorophenyl)ethoxymethyl]piperidine hydrochloride;

4-phenyl-4-[2,3-(dimethoxy)benzyloxymethyl]piperidine hydrochloride;

5-[4-(3-isopropoxy)benzyloxymethyl-4-phenyl-piperidin-1-ylmethyl]2,4-dihydro-[1,2,4]-triazol-3-one;

4-[3-(trifluoromethoxy)benzyloxymethyl]-4-phenylpiperidine hydrochloride;

(+)5-[4-(1-[3-bromophenyl]-ethoxymethyl)-4-phenylpiperidin-1-ylmethyl]-2,4-dihydro-[1,2,4]-triazol-3-one;

(−)5-[4-(1-[3-bromophenyl]-ethoxymethyl)-4-phenylpiperidin-1-ylmethyl]-2,4-dihydro-[1,2,4]-triazol-3-one;

and salts thereof; and more especially the pharmaceutically acceptable salts thereof.

For use in medicine, the salts of the compounds of formula (I) will be pharmaceutically acceptable salts. Other salts may, however, be useful in the preparation of the compounds according to the invention (such as the dibenzoyltartrate salts) or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, sulphuric acid, fumaric acid, maleic acid, succinic acid, acetic acid, citric acid, tartaric acid, carbonic acid, phosphoric acid or p-toluenesulphonic acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

Favoured salts of the compounds according to the invention are acid addition salts of pharmaceutically acceptable acids.

Preferred salts of the compounds according to the invention include the hydrochloride and p-toluenesulphonic acid salts.

The invention also provides pharmaceutical compositions comprising one or more compounds of this invention in association with a pharmaceutically acceptable carrier. Preferably these compositions are in unit dosage forms such as tablets, pills, capsules, powders, granules, solutions or suspensions, or suppositories, for oral, parenteral or rectal administration, or topical administration including administration by inhalation or insufflation.

The invention further provides a process for the preparation of a pharmaceutical composition comprising a compound of formula (I), or a salt or prodrug thereof, and a pharmaceutically acceptable carrier, which process comprises bringing a compound of formula (I), or a salt or prodrug thereof into association with a pharmaceutically acceptable carrier.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention, for example 1 to 100 mg. The tablets or pills of the novel composition can coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

For topical administration, for example as a cream, ointment or lotion, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as MS and ALS and other neuropathological disorders such as peripheral neuropathy, including diabetic and chemotherapy-induced neuropathy, and postherpetic and other neuralgias; small cell carcinomas such as small cell lung cancer; respiratory diseases, particularly those associated with excess mucus secretion such as chronic obstructive airways disease, bronchopneumonia, chronic bronchitis, cystic fibrosis and asthma, and bronchospasm; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atropic dermatitis, urticaria, and other eczematoid dermatitis; addiction disorders such as alcoholism; stress related somatic disorders; reflex sympathetic dystrophy such, as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; emesis, including acute, delayed and anticipatory emesis, for example, induced by chemotherapy, radiation, toxins, pregnancy, vestibular disorders, surgery, migraine and variations in intracranial pressure; disorders of bladder function such as bladder detrusor hyper-reflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine, visceral pain and post operative pain.

The compounds of formula (I) are particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and especially migraine and post operative pain.

The compounds of the formula (I) are useful in treating more than one symptom at a time, for example emesis and pain following surgery.

The present invention further provides a compound of formula (I), or a salt or prodrug thereof, for use in therapy.

According to a further or alternative aspect, the present invention provides a compound of formula (I) or a pharmaceutically acceptable salt thereof for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a pharmaceutically acceptable salt thereof or a composition comprising a compound of formula (I) or a pharmaceutically acceptable salt thereof.

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor antagonist or tachykinin antagonist which acts at NK-2 receptors. The compound of formula (I) and the bronchodilator may be administered to a patient simultaneously, sequentially or in combination.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

In the treatment of the conditions associated with an excess of tachykinins, a suitable dosage level is about 0,001 to 50 mg/kg per day, in particular about 0.01 to about 25 mg/kg, such as from about 0.05 to about 10 mg/kg of a compound of formula (I) per day. For example, in the treatment of conditions involving the neurotransmission of pain sensations, a suitable dosage level is about 0.001 to 25 mg/kg per day, preferably about 0.005 to 10 mg/kg per day, and especially about 0,005 to 5 mg/kg per day. The compounds may be administered on a regimen of 1 to 4 times per day, preferably once or twice per day.

The compounds according to the invention may be prepared by a process which comprises reacting a compound of formula (II) with a compound of formula (III):

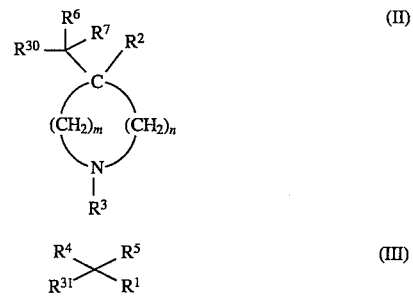

wherein $R^1$, $R^2$, $R^4$, $R^5$, $R^6$, $R^7$, m and n are as defined for formula (I), $R^3$ is as defined for formula (I) except that, when $R^3$ is H it is replaced by a suitable protecting group, such as $CO_2(C_{1-6}alkyl)$; and one of $R^{30}$ and $R^{31}$ represents a leaving group and the other of $R^{30}$ and $R^{31}$ represents XH, where X is as defined for formula (I); in the presence of a base, followed by deprotection, if required.

Suitably $R^{30}$ represents XH and $R^{31}$ represents a leaving group.

Suitable leaving groups include halo, e.g. chloro, bromo or iodo, or sulphonate derivatives such as tosylate or mesylate.

The reaction is conveniently carried out in a suitable organic solvent, such as an ether, e.g. 1,2-dimethoxyethane, at a temperature in the region of 0° C. Favoured bases of use in the reaction include alkali metal amides and hydrides, such as potassium bis(trimethylsilyl)amide or potassium hydride. Suitably, potassium bis(trimethylsilyl)amide is used.

Compounds of formula (I) may also be prepared from different compounds of formula (I) by interconversion processes. In particular, interconversion processes may be used to vary the group $R^3$. For example, compounds of formula (I) wherein $R^3$ is other than H may be prepared from the corresponding compounds of formula (I) wherein $R^3$ is H by conventional methods, such as reaction with a compound $R^3$-Hal, where Hal represents halo, in the presence of a base. Suitable reagents and conditions will be readily apparent to those skilled in the art and are illustrated by the accompanying Examples. It will be appreciated therefor that compounds of the formula (I) wherein $R^3$ is H are highly favoured compounds of this invention since in addition to possessing useful biological activity they are of use as intermediates. Suitable bases include organic bases, such as tertiary amines, e.g. triethylamine, and inorganic bases, such as alkali metal carbonates, e.g. sodium carbonate. Compounds of formula (I) wherein $R^3$ is $COR^9$ may also be prepared from compounds of formula (I) wherein $R^3$ is H by, for example, reaction with an appropriate acid anhydride. Compounds of formula (I) wherein $R^3$ is $C_{1-6}alkyl$ may be prepared from corresponding compounds of formula (I) wherein $R^3$ is $COR^9$ by reduction using, for example, borane or a borohydride such as sodium cyanoborohydride. Suitable procedures will be readily apparent to those skilled in the art. Compounds of formula (I) wherein $R^3$ is $C_{1-6}$ alkyl substituted by $CONR^{10}R^{11}$ may be prepared from corresponding compounds of formula (I) wherein $R^3$ is $C_{1-6}$alkyl substituted by $CO_2R^{10}$ by treatment with ammonia or an amine of formula $NR^{10}R^{11}$.

The intermediates of formula (II) above wherein $R^{30}$ is SH may be prepared from the corresponding intermediates of formula (II) wherein $R^{30}$ represents OH by treating the latter compound with Lawesson's reagent or phosphorus pentasulphide in a suitable solvent, e.g. pyridine, at ambient or elevated temperatures, suitably at reflux temperature.

Intermediates of formula (II) above wherein $R^{30}$ is OH and $R^6$ and $R^7$ both represent H may be prepared from corresponding compounds of formula (IV):

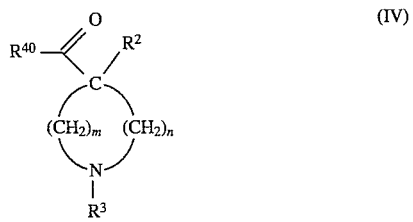
(IV)

wherein $R^2$, $R^3$, m and n are as defined for formula above and $R^{40}$ represents hydroxy, alkoxy or amino, by apparent to one skilled in the art and include, for example, metallic hydrides, such as lithium hydride.

Intermediates of formula (II) wherein $R^{30}$ is OH and one of $R^6$ and $R^7$ is $C_{1-6}$alkyl and the other of $R^6$ and $R^7$ is H may be prepared from compounds of formula (IV) wherein $R^{40}$ is H, by reaction with a Grignard reagent of formula $MgHalR^6$ or $MgHalR^7$, wherein $R^6$ and $R^7$ are as previously defined and Hal is halo such as chloro, bromo or iodo. Intermediates of formula (II) wherein $R^{30}$ is OH and both of $R^6$ and $R^7$ represent $C_{1-6}$alkyl may be prepared from compounds of formula (IV) wherein $R^{40}$ is alkoxy by reaction with Grignard reagents of formulae $MgHalR^6$ and $MgHalR^7$, as above defined. Suitabel reaction conditions will be readily apparent to those skilled Compounds of formula (IV) wherein $R^{40}$ is H may be prepared from compounds of formula (IV) wherein $R^{40}$ is alkoxy or amino by reduction. Suitable reducing agents will be readily apparent to those skilled in the art and include, for example, where $R^{40}$ is alkoxy, diisobutylaluminium hydride, and, where $R^{40}$ is amino, lithium aluminium hydride.

Intermediates of formula (II) wherein $R^{30}$ is a leaving group may be prepared from compounds of formula (II) wherein $R^{30}$ is OH, for example, by reaction with a thionyl halide, a mesyl halide or a tosyl halide.

Where they are not commercially available, the intermediates of formula (III) above may be prepared by the procedures described in the accompanying Examples or by alternative procedures which will be readily apparent to one skilled in the art.

Compounds of formula (IV) are commercially available, or may be prepared by known procedures.

For example, suitable methods for the preparation of compounds of formula (IV) are described in European Patent Application no. 0 337 167, *J. Am. Chem. Soco*, 81, 1201 (1959), *J. Med. Chem.*, 17, 453 (1974) and *J. Med. Chem.*, 24, 218 (1981).

In general, compounds of formula (IV) wherein $R^3$ is H, $R^{40}$ is alkoxy and n is 0 may be prepared by cyclisation of an intermediate of formula (V)

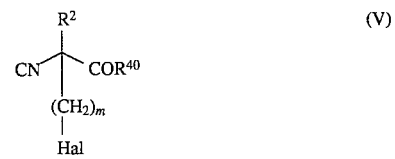
(V)

wherein $R^2$, $R^{40}$ and m are as previously defined and Hal represents halo, for example, chloro or bromo, in the presence of a base.

Suitable bases of use in the reaction include tertiary amines, such as, for example, triethylamine. The reaction is conveniently effected in a suitable organic solvent, such as an ether, for example, tetrahydrofuran, suitably at elevated temperature, such as the reflux temperature of the chosen solvent.

Intermediates of formula (V) may be prepared by reaction of compounds of formula (VI) with compounds of formula (VII)

wherein $R^2$, $R^{40}$, m and Hal are as previously defined, in the presence of a base.

Suitable bases of use in the reaction include alkali metal hydrides, such as, for example, sodium hydride. The reaction is conveniently effected in a suitable organic solvent, such as an ether, for example, tetrahydrofuran, suitably at elevated temperature, such as the reflux temperature of the chosen solvent.

Compounds of formulae (VI) and (VII) are commercially available, or may be prepared from commercially available starting materials using conventional procedures well known to those skilled in the art.

Compounds of formula (IV) wherein $R^{40}$ is alkoxy and n is other than 0 may in general be prepared from the corresponding compounds of formula (VIII)

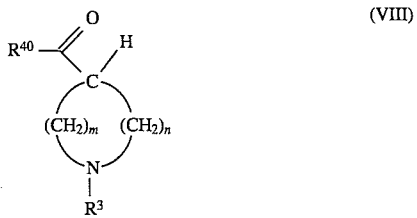
(VIII)

wherein $R^3$, $R^{40}$ and m are as previously defined and n is 1 or 2 by treatment with a base and reaction of the resulting nucleophile with a reagent suitable to introduce the group $R^2$, such as an activated aryl moiety, for example

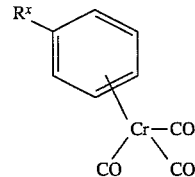

wherein $R^x$ is H or halo, such as chloro; an aryliodide in the presence of nickle bromide (*J. Am. Chem. Soc.*, 99, 833 (1977)); or a hypervalent aryliodide (*Synthesis*, 709 (1984)).

Compounds of formula (VIII) may be prepared from the corresponding intermediates of formula (IX)

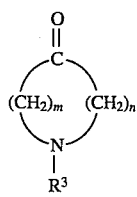

wherein $R^3$, m and n are as defined for formula (VIII) by conventional methods, for example, by sequential reaction with 1,3-dithiane and an alcohol of formula $R^{40}H$, where $R^{40}$ is alkoxy, in the presence of an acid, such as a mineral acid, for example, hydrochloric acid.

Still further procedures suitable for the preparation of compounds of formula (IV) will be readily apparent to those skilled in the art.

Compounds of the formula (I) wherein $R^4$ is a $C_{1-6}$ alkyl group and $R^5$ is hydrogen may be prepared by reduction or a corresponding compound of the formula (I) wherein $R^4$ and $R^5$ together with the carbon to which that are attached represent a $C=C(R^{41})R^{51}$ group wherein $R^{41}$ and $R^{51}$ are independently hydrogen or alkyl of 1 to 5 carbon atoms. Such compounds of formula (I) may be prepared from the corresponding compound of formula (I) wherein $R^4$ is hydrogen and $R^5$ is hydrogen by the method of P. Kocienski and M. Mortimore, T. Lett., 29 (27), 3375–3360, 1988. More suitably $R^{41}$ is hydrogen. More suitably $R^{51}$ is hydrogen. Most suitably this process is adapted to the preparation of a compound of the formula (I) wherein $R^4$ is methyl and $R^5$ is hydrogen.

Where the above-described process for the preparation of the compounds according to the invention gives rise to mixtures of stereoisomers these isomers may, if desired, be separated, suitably by conventional techniques such as preparative chromatography.

The novel compounds which contain one or more chiral centres may be prepared in racemic form, or individual enantiomers may be prepared either by enantiospecific synthesis or by resolution. For example, intermediate alcohols of formula (II), wherein $R^{30}$ is OH, may be resolved into their component enantiomers by standard techniques, such as the formation of diastereomeric esters or amides, followed by chromatographic separation or separation by fractional crystallization and removal of the chiral auxiliary. The diastereomeric alcohols can then be used to prepare optically pure compounds of formula (I).

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

Using test methods described in PCT/GB92/01212 (International Publication No. WO 93/01159) pages 30–33, it was found that the compounds referred to in the Examples hereinafter had $IC_{50}$ at NKIR of less than 500 nM.

The following illustrate pharmaceutical compositions according to the invention.

|  | Amount mg | | |
|---|---|---|---|
| Tablets containing 1–25 mg of compound | | | |
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |
| Tablets containing 26–100 mg of compound | | | |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

| Parenteral injection | |
|---|---|
| | Amount mg |
| Compound of formula (I) | 1 to 100 mg |
| Citric Acid Monohydrate | 0.75 mg |
| Sodium Phosphate | 4.5 mg |
| Sodium Chloride | 9 mg |
| Water for Injections | to 1 ml |

The sodium phosphate, citric acid monohydrate and sodium chloride are dissolved in a portion of the water. The compound of formula (I) is dissolved or suspended in the solution and made up to volume.

| Topical formulation | |
|---|---|
| | Amount mg |
| Compound of formula (I) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

The following Examples illustrate the preparation of compounds according to the invention.

EXAMPLE 1

1-t-Butoxycarbonyl-4-phenyl-4-[(3,5-bistrifluoromethyl) benzyloxymethyl]piperidine a) 4-Phenyl-4-carboxy piperidine tosylate (10 g) was added portionwise to a solution of lithium aluminium hydride (1.52 g) in dry tetrahydrofuran (100 ml) at 0° C. After addition was complete the reaction mixture was warmed to reflux for 30 min and then allowed to cool to room temperature. The reaction was then quenched by addition of 2N sodium hydroxide solution until a white granular precipitate formed. The mixture was filtered and the filtrate extracted with ethyl acetate (200 ml), dried (MgSO$_4$), filtered and solvent removed to afford a clear oil. The residual oil was taken up in dichloromethane (50 ml) and di-t-butyl-dicarbonate (1.9 g) added. The resulting mixture was stirred at room temperature for 18 h. Solvent removed and the residual oil subjected to flash chromatography on silica gel to afford 1-t-butoxycarbonyl-4-phenyl-4-hydroymethyl piperidine as a colourless oil (2.1 g). $^1$H NMR (360 MHz, CDCl$_3$) 1.43 (9H, s, C(CH$_3$)$_3$, 1.75 (2H, td, J=11.0, 10 Hz, NCH$_2$CH$_2$), 2.17 (2H, m, NCH$_2$), 3.05 (2H, td, J=11.0, 1.0 Hz, NCH$_2$CH$_2$), 3.55 (2H, s, CH$_2$—OH), 3.73 (2H, m, NCH$_2$), 7.24–7.41 (5H, m, ArH); m/z (CI$^+$) 292 (M$^+$+1).

b) Sodium hydride (120 mg×60%) was added to a stirred solution of 1-$^t$butoxycarbonyl-4-phenyl-4-hydroxymethyl piperidine (760 mg), and 3,5-bistrifluoromethylbenzylbromide (801 mg), in dry dimethylformamide (5 ml). The resulting solution was stirred for 18 hours at room temperature, poured into water (100 ml)and extracted into ethyl acetate (50 ml). The organic extract was washed with water (3×50 ml), brine (2×50 ml), dried (MgSO$_4$), filtered and the solvent removed to afford a yellow oil. Purification by flash chromatography on silica gel using 15% ethyl acetate/n hexane as eluant, afforded 1-$^t$butoxycarbonyl-4- phenyl-4-[(3,5-bistrifluoromethyl)benzyl oxymethyl]piperidine as a clear oil (900 mg). $^1$H NMR (360 MHz, CDCl$_3$) 1.46 (9H, s, C(CH$_3$)$_3$), 1.86 (2H, td, J=10.0, 1.0 Hz, NCH$_2$CHH ×2), 2.21 (2H, m, HHCNCHH), 3.03 (2H, td, J=10.0, 1.0 Hz, NCH$_2$CHH×2), 3.45 (2H, s, CH$_2$—O—CH$_2$Ar), 3.76 (2H, m, HHCNCHH), 4.43 (2H, s, CH$_2$—OCH$_2$Ar), 7.24 (2H, m, ArH×2), 7.33 (3H, m, ArH×3), 7.54 (2H, s, C—C H—CCF$_3$×2), 7.73 (1H, s, CF$_3$—C—CH—CCF$_3$); m/z (CI$^+$) 518 (M$^+$+1).

EXAMPLE 2

4-Phenyl-4-[(3,5-bistrifluoromethyl)benzyloxymethy]piperidine hydrochloride

1-$^t$Butoxycarbonyl-4-phenyl-4-[(3,5-bistrifluoromethyl) benzyoxymethyl]piperidine (900 mg) was dissolved in dry diethyl ether and a stream of dry hydrogen chloride gas poured through the solution for 30 mins. The solution was stirred for a further 2.5 h at room temperature, at which point the solvent was removed under reduced pressure to afford a white solid. Recrystallisation from ethyl acetate afforded 4-Phenyl-4-[(3,5-Bistrifluoromethyl)benzyl oxymethyl]piperidine hydrochloride as a white amorphous solid (260 mg); mp 139°–141° C. $^1$H NMR (250 MHz, DMSO-d$_6$) 2.08 (2H, m, N—CH$_2$CHH×2), 2.19 (2H, m, HHC—NCHH), 2.73 (2H, m, NCH$_2$—CHH ×2), 3.21 (2H, m, HHC—N—CH H), 3.49 (2H, s, CH$_2$—OCH$_2$Ar), 4.58 (2H, s, CH$_2$—OC H$_2$Ar), 7.27 (5H, m, ArH), 7.77 (2H, C—CH—CF$_3$×2), 7.98 (1H, s, CF$_3$C—CH—CCF$_3$); m/z (CI$^+$) (M$^+$+1). C$_{21}$H$_{21}$NOF$_6$.HCl requires C, 55.57; H, 4.88; N, 3.08 Found C, 55.39; H, 4.88; N, 3.13%.

EXAMPLE 3

2-[(3,5-Bis-trifluoromethyl)benzyl]oxymethyl-2-phenyl pyrrolidine a) Lithium aluminium hydride (1M in tetrahydrofuran; 10.6 ml) was added to a cooled (0° C.) suspension of (±)-2-phenylproline hydrochloride (0.85 g) and the mixture heated at reflux for 1.5 h. After cooling to 0° C., water (1 ml) was added followed by 2M NaOH (1 ml) and water (2 ml). The reaction mixture was diluted with ethyl acetate (50 ml) then filtered through a pad of Hi-flo and the residue concentrated in vacuo to give (±)-2-phenylprolinol as a yellow oil which solidified on standing. $^1$H NMR (250 MHz, CDCl$_3$) d 7.42–7.20 (5H, m, ArH), 3.60 (1H, d, J=10.0 Hz, CHHOH), 3.49 (1H, d, J=10.0 Hz, CHHOH), 3.07 (2H, t, J=5.7 Hz, CH$_2$N), 2.43 (2H, br s, OH and NH), 2.19–1.75 (4H, m).

b) A solution of 2-phenylprolinol (0.51 g) and di-t-butyldicarbonate (0.66 g) in dichloromethane (4 ml) was stirred at 23° C. for 16 h. Evaporation of the solvent in vacuo provided 1-t-butyloxycarbonyl-2-phenylprolinol as an oil. $^1$H NMR (360 MHz, CDCl$_3$) d 7.36–7.17 (5H, m, ArH), 5.27 (1H, d, J=7.2 Hz, CHHOH), 4.27 (1H, t, J=7.6 Hz), 3.94 (1H, d, J=7.2 Hz, CHHOH), 3.66 (1H, 5, J =7.4 Hz), 3.51 (1H, m), 1.94 (2H, m), 1.8–1.66 (2H, m), 1.50 (9H, s). $^{13}$C NMR (90.6 MHz, CDCl$_3$) d 156.3, 141.9, 128.3, 126.6, 126.0, 80.4, 71.8, 66.9, 49.1, 40.1, 28.5, 20.9.

c) Sodium hydride (80% in oil, 52 mg) was added to a solution of 1-t-butoxycarbonyl-2-phenylprolinol (370 mg) and 3,5-bis-(trifluoromethyl)benzyl bromide (0.366 ml) in dry N,N-dimethylformamide (1 ml) and the mixture was stirred at 23° C. for 18 h. Water (20 ml) was added and the mixture extracted with ethyl acetate (3×20 ml). The combined organic phases were washed with brine (1×10 ml) then dried (MgSO$_4$) and concentrated to leave a yellow oil. Purification by chromatography on silica gel using hexane-ethyl acetate(19:1 then 9:1 then 4:1 ) as eluant provided 1-t-butyloxycarbonyl-2-((3,5-bis-trifluoromethyl)benzyloxymethyl)-2-phenyl pyrrolidine as a white solid. $^1$H NMR (250 MHz, CDCl$_3$) d 7.84 (3H, app d), 7.26 (5H, m), 4.70 (2H, d, J=8.4 Hz), 4.38 (0.5H, d, J=9.8 Hz), 4.18 (0.5H, d, J=8.4 Hz), 4.12 (0.5H, d, J=8.4 Hz), 3.97 (0.5H, d, J=9.8 Hz), 3.85–3.44 (2H, m), 2.57 (1H, m), 2.06 (1H, m), 1.94–1.56 (2H, m), 1.43 (5H, s), 1.14 (4H, s).

d) A solution of the product of part c) (0.1 g) in trifluoroacetic acid (2 ml) was stirred at 23° C. for 10 min. Excess solvent was removed in vacuo and the residue partitioned between dichloromethane and 2M sodium hydroxide solution. The layers were separated, and the aqueous phase extracted once with dichloromethane. The combined organic phases were dried (K$_2$CO$_3$) and concentrated to leave a colourless, viscous oil. The HCl salt was prepared (HCl in methanol and recrystallised from hexane-ether, to give 2-((3, 5-bis-trifluoromethyl)-benzyloxymethyl)-2-phenyl pyrrolidine hydrochloride salt, mp=152°–155° C. $^1$H NMR (360 MHz, CD$_3$OD) d 7.99 (1H, s), 7.68 (2H, s), 7.54–7.37 (5H, m), 4.70 (d, J=14 Hz), 4.62 (d, J=14 Hz), 3.90 (d, J=7 Hz), 3.84 (d, J=7 Hz), 3.38 (2H, m), 2.48 (1H, m), 2.26 (1H, m), 2.10 (1H, m), 1.97 (1H, m). MS (CI$^+$) m/z 404 (MH, 100%).

The following Examples were prepared following the procedures of Examples 1 and 2.

EXAMPLE 4

4-Phenyl-4-(2-trifluoromethyl)benzyloxymethyl piperidine hydrochloride

Mpt=181° C.; $^1$H NMR (360 MHz, DMSO-d$_6$) d 2.07–2.21 (2H, m), 2.28–2.39 (2H, m), 2.64–2.78 (2H, m), 3.12–3.23 (2H, m), 3.51 (2H, s), 4.53 (2H, s), 7.24–7.72 (9H, m), 9.00 (2H, br). MS, CI$^+$, 350 (M$^+$); C$_{20}$H$_{22}$F$_3$NO.HCl requires C, 62.26; H, 6.01; N, 3.63; found C, 61.92, H, 5.97; N, 3.66.

EXAMPLE 5

4-Phenyl-4-benzyloxymethylpiperidine hydrochloride

Mpt=156° C.; $^1$H NMR (360 MHz, DMSO-d$_6$) d 2.06–2.18 (2H, m), 2.27–2.39 (2H, m), 2.62–2.76 (2H, m), 3.09–3.21 (2H, m), 3.41 (2H, s), 4.38 (2H, s), 7.13–7.46

(10H, m), 9.05 (2H, br); MS, CI⁺, 282 (M⁺); C₁₉H₂₃NO.HCl.1.8H₂O requires C, 68.31; H, 7.78; N, 4.19; found C, 68.34; H, 7.58; N, 4.23.

EXAMPLE 6

4-Phenyl-4-(3-chloro-5-ᵗbutyl)benzyloxymethylpiperidine hydrochloride

Mpt=75° C., ¹H NMR (360 MHz, DMSO-d₆), d 1.24 (9H, s), 2.04–2.15 (2H, m), 2.30–2.38 (2H, m), 2.67–2.77 (2H, m), 3.12–3.20 (2 H, m), 3.43 (2H, s), 4.40 (2H, s), 6.98 (1H, s), 7.11 (1H, s), 7.24–7.31 (2H, m), 7.36–7.46 (4H, m), 9.02 (2H, br). C₂₃H₃₀ClNO.HCl requires C, 67.74; H, 7.65; N, 3.43 found C, 67.38; H, 7.95; N, 3.26.

EXAMPLE 7

4-Phenyl-4-(3,5-dichlorobenzyloxymethyl)piperidine hydrochloride

Mpt=180° C. ¹H NMR (360 MHz, DMSAO-d₆) d 2.04–2.14 (2H, m), 2.07–2.19 (2H, m), 2.66–2.77 (2H, m), 3.12–3.22 (2H, m), 3.41 (2H, s), 4.40 (2H, s), 7.11 (2H, s), 7.21–7.47 (6H, m); MS (CI⁺), 350,352 (M⁺); C₁₉H₂₁Cl₂NO.1.5 HCl requires C, 56.35; H, 5.60; N, 3.45. Found C, 56.71; H, 5.49; N, 3.38%.

EXAMPLE 8

4-Phenyl-4-(3-trifluoromethylbenzyloxymethyl)piperidine hydrochloride

Mpt=194°–195° C. ¹H NMR (360 MHz, DMSO-d₆) d 2.06–2.18 (2H, m), 2.30–2.40 (2H, m), 2.66–2.79 (2H, m), 3.11–3.21 (2H, m), 3.46 (2H, s), 4.49 (2H, s), 7.26–7.64 (8H, m) 8.82–9.08 (1H, b), 9.11–9.25 (1H, b); MS, CI⁺, 350 (M⁺). C₂₀H₂₂F₃NO.HCl requires C, 62.226; H, 6.01; N, 3.63. Found C, 62.33; H, 6.08; N, 3.75.

EXAMPLE 9

4-Phenyl-4-(4-trifluoromethylbenzyloxymethyl)piperidine hydrochloride

Mpt=113° C. ¹H NMR (360 MHz, DMSO-d₆) d 2.09–2.20 (2H, m), 2.30–2.42 (2H, m), 2.64–2.80 (2H, m), 3.13–3.22 (2H, m), 3.46 (2H, s), 4.52 (2H, s), 7.26–7.49 (7H, m), 7.61–7.69 (2H, d, J=8.1 Hz), 8.96–9.06 (1H, b), 9.15–9.21 (1H, b); MS, CI⁺, 350 (M⁺+1). C₂₀H₂₂F₃NO.1.5HCl.H₂O requires C, 56.91; H, 6.09; N, 3.32. Found C, 56.79; H, 6.14; N, 3.38.

EXAMPLE 10

1-Acetyl-4-phenyl-4-(3,5-bis(trifluoromethyl)benzyloxymethyl)piperidine

Acetyl chloride (86 mg) was added to a stirred solution of the compound of Example 2 (500 mg) and triethylamine (310 ml) in dry dichloromethane at 0° C. The resulting solution was allowed to warm to room temperature overnight. The reaction mixture was diluted with water (50 ml) and the organic layer separated. The aqueous layer was extracted with dichloromethane, and the combined organic extracts washed with 1N sodium hydroxide solution, dried (MgSO₄), filtered and the solvent removed under reduced pressure to afford a clear oil. Recrystallisation from hexane/ ether afforded the product as white needles. mpt=64–65° C.; ¹H NMR (360 MHz, DMSO-d₆) d 1.70–1.80 (1H, m), 1.81–1.91 (1H, m), 1.97 (3H, s), 2.04–2.22 (2H, br m), 2.90–2.99 (1H, m), 3.09–3.19 (1H, m), 3.51 (2H, s), 3.55–3.63 (1H, m), 3.80–3.89 (1H, m), 4.55 (2H, s), 7.20–7.45 (5H, m), 7.75 (2H, s), 7.96 (1H, s). MS, CI⁺, 460 (M⁺). C₂₃H₂₃F₆NO₂.0.25H₂O requires C, 59.55; H, 5.10; N, 3.02 found C, 59.68; H, 4.88; N, 2.90.

EXAMPLE 11

1-Methanesulphonyl-4-phenyl-4-(3,5-bis(trifluoromethyl)benzyloxymethyl)piperidine The title compound was prepared analogously to the preparation of Example 10: mpt=102°–104° C., ¹H NMR (360 MHz, DMSO-d₆) d 1.97–2.08 (2H, m), 2.36–2.46 (2H, m), 2.66 (3H, s), 2.80–2.90 (2H, m), 3.44 (2H, s), 3.55–3.64 (2H, m), 4.44 (2H, s), 7.24–7.44 (5H, m), 7.52 (2H, s), 7.73 (1H, s). MS, CI⁺, 496 (M⁺), 513 (M+NH₄)⁺. C₂₂H₂₃F₆NO₃S requires C, 53.33; H, 4.68; N, 2.83 found C, 53.06; H, 4.93; N, 2.73.

EXAMPLE 12

5-[(4-(3,5-Bis-trifluoromethyl-benzyloxymethyl)-4-phenyl-piperidine-1-ylmethyl]-2,4-dihydro-[1,2,4]-triazol-3-one a) Sodium methoxide (400 mg) was added to a stirred solution of chloroacetonitrile (20 g) in dry methanol (120 ml). The resulting solution was stirred for 1 hour at room temperature, and then neutralised by the addition of acetic acid. ᵗButyl carbazate (35 g) was then added and stirring continued for a further 1 hour. The solvent was then removed under reduced pressure and the residue taken up in ethyl acetate, washed with water, the organic layer separated and dried (MgSO₄). Filtration and removal of solvent gave a white solid. Recrystallisation from isopropanol afforded N-t-Butoxycarbonyl chloromethyl imidrazone as white needles (31 g). mpt=69°–70° C.; ¹H NMR (360 MHz, CDCl₃) δ1.24 (9H, s, C(CH₃)₃), 4.00 (2H, s, Cl—CH₂—), 5.6 (2H, bs, NH₂), 8.7 (1H, bs, NH—CO).

b) The product of part a) (7.1 g) was added to a stirred suspension of the compound of Example 2 (15.0 g) in dry DMF (50 ml) and the resulting solution stirred for 24 hours at room temperature. The reaction mixture was poured into water and the aqueous mixture extracted into ethyl acetate. The organic extract was washed exhaustively with water, and finally brine, dried (MgSO₄), filtered and the solvent removed to afford a yellow solid. The recovered material was re-dissolved in dry toluene and warmed to reflux for 30 minutes in the presence of a catalytic amount of potassium t-butoxide. The solvent was removed under reduced pressure and the residue purified by chromatography on silica gel (15% EtOAc/nHex) to afford the product as a white powder (17.2 g). The recovered product was taken up in dry ether and HCl gas passed through the solution. The product crystallised as a white powder on stirring (18.1 g). mp=159°–160° C. ¹H NMR (360 MHz, CDCl₃) δ2.1 (2H, m, NCH₂CHHx2), 2.23 (2H, m, HHC—NCHH), 2.61 (2H, m, NCH₂CHHx2), 2.93 (2H, m, HHCNCHH), 3.36 (2H, s, CH₂OCH₂Ar), 3.80 (1H, d, J=15 Hz, NCHH—Met), 4.1 (1H, d, J=15.0 Hz, NCHH—Met), 4.2 (2H, s, CH₂OC H₂Ar), 7.1–7.25 (5H, m, ArH), 7.76 (2H, s, C—C H—CF₃x2); m/z (CI⁺) 515 (M⁺+1). C₂₄H₂₄N₄O₂F₆.HCl H₂O requires C, 50.66; H, 4.78; N, 9.84 Found C, 50.30; H, 4.49; N, 9.55%.

EXAMPLE 13

2-[1'-Imidazolyl]acetyl-4-phenyl-4[(3,5-bistrifluoromethyl]11 benzyloxymethyl]piperidine tosylate a) The compound of Example 2 (1.36 g) was stirred with triethylamine (836 μl) in anhydrous dichloromethane (70 ml) under an inert atmosphere for 15 minutes. Bromoacetyl bromide (382 μl) was added by syringe in one portion and the reaction mixture stirred for 2.5 hours at room temperature. The solution was washed sequentially with 40 ml aliquots of 2N HCl, 0.4M NaHCO$_3$ and water, dried (MgSO$_4$) and evaporated to a brown gum (1.8 g). The recovered material was purified by flash silica gel chromatography in ethyl acetate/petrol (2:3) to afford a colourless oil, 1.0 g. $^1$H NMR (360 MHz, CDCl$_3$) δ7.74 (1H, s, A–H Ar), 7.54 (2H, s, 2-H and 6-H Ar), 7.36–7.42 (4H, m) and 7.27–7.31 (1H, m, Ph), 4.45 (2H, s, OCH$_2$Ar), 4.22 (1H, dt, J=13.7 and <3 Hz, CHHNCHH), 4.05 and 3.85 (2H total, 2×2, COCH$_2$Br), 3.69 (1H, dt, J=13.6 and <3 Hz, CHHNCHH), 3.46 (2H, s, CH$_2$OBr), 3.27 (1H, dt, J=12.5 and 2.7 Hz, CHHCHH), 2.98 (1H, dt, J=12.5 and 3.0 Hz, CHHNCHH), 2.26–2.43 (2H, bm, CHH.C.CHH), 1.85–2.04 (2H, m, CHH.C.CHH). m/z (CI$^+$) 538, 540 (M+1, 1:1, 45%), 460 (M—Br+2H, 100%).

b) The compound of step a) (225 mg) was stirred with sodium imidazole (45 mg) in anhydrous dimethylsulphoxide (2.5 ml) under an inert atmosphere for 2 hours at 60° C. The cooled solution was diluted with water (10 ml) and extracted with ethyl acetate (4×10 ml). The combined organic extracts were washed once with a saturated brine solution (10 ml), dried (Na$_2$SO$_4$) and evaporated to dryness (180 mg). The crude residue was purified by flash silica gel chromatography in dichloromethane-methanol (18:1) to yield the title compound as its free base (85 mg). Treatment with one equivalent of pTSA in ether afforded the title compound as a white powder. mp 197.5°–199.5° C. $^1$H NMR (360 MHz, d$_6$-DMSO) δ8.95 (1H, s, H-2 imid.), 7.98 (1H, s, 4-H Ar), 7.76 (2H, s, 2-H and 6-H Ar), 7.63 and 7.58 (2×1H, 2×d, J<3 Hz, H-4 and H-5 imid.), 7.45–7.49 (4H, m, 2H(Ph) and H (Tol)), 7.37 (2H, t, J=7.6 Hz, 2H Ph), 7.25 (1H, t, J=7.2 Hz, 4-H Ph), 7.10 (2H, d, J=7.7 Hz, 2H Tol), 5.36 (1H, d, J=16.6 Hz) and 5.23 (1H, d, J=16.6 Hz, OCH$_2$Ar), 4.57 (2H, s, COCH$_2$N), 3.85 (1H, dt, J=13.4 and <4 Hz) and 3.56 (1H, dt, J=13.4 and <3 Hz, CHHNCHH), 3.32 (2H, s, CH$_2$OBr), 3.20 (1H, bt, J=10.4 Hz) and 3.04 (1H, bt J=10.3 Hz, CH HNCHH), 2.28 (3H, s, CH$_3$), 2.15–2.30 (2H, bm, C HH.C.CHH), 1.97 (1H, bt, J=10.2 Hz) and 1.83 (1H, bt, J=10.1 Hz, CHH.C.CHH). m/z (CI$^+$) 526 (M+1, 72%) 298 (76%). C$_{26}$H$_{25}$F$_6$N$_3$O$_2$.C$_7$H$_8$O$_3$S requires: C, 56.81; H, 4.77; N, 6.02; Found C, 56.99; H, 4.50; N, 5.87%.

EXAMPLE 14

5-[4-(3,5-Bistrifluoromethylbenzyloxymethyl)-4-(4-fluorophenyl)-piperidin-1-ylmethyl]-2,4-dihydro[1,2,4]-triazol-3-one a) 4-Fluorophenyl acetic acid (25 g) was dissolved in anhydrous methanol, stirred under nitrogen and cooled in an ice/methanol bath. Dry HCl gas was bubbled through the reaction for 1 hr. The methanol was removed by rotary evaporator, the residue was dispersed between aqueous sodium hydrogen carbonate and dichloromethane. The organic layer was washed with brine, dried (MgSO$_4$) and concentrated to afford a clear oil (24.4 g). $^1$H NMR (360 MHz, CDCl$_3$) δ$_H$ 3.61 (2H, s, CH$_2$), 3.70 (3H, s, CH$_3$), 6.97–7.06 (2H, m, ArH), 7.20–7.27 (2H, m, ArH). MS m/z CI$^+$169 (M+1$^+$, 100%).

b) The 4-fluorophenyl methyl acetate (24.4 g) was dissolved in dry dimethyl sulphoxide (150 ml) and added via a dropping funnel to sodium hydride (80% wt 15.7 g) under nitrogen. After the slow addition was complete the dianion was left to form over a period of 20 mins. Mechlorethamine hydrochloride (24 g) was dissolved in dry dimethyl sulphoxide (125 ml) and placed in a dropping funnel and added to the dianion over a period of 20 mins. The reaction was poured onto ice (2 dm$^3$) and left overnight. The aqueous mixture was extracted with diethyl ether (50×250 ml), the combined organics were acidified with 5N HCl (1 dm$^3$). The aqueous layer was basified using potassium carbonate and extracted with ethyl acetate (3×250 ml). The combined organics were dried (MgSO$_4$) and concentrated in vacuo to afford a brown oil. The oil was purified by flash chromatography eluted with 100% EtOAc graduated to 8% methanol in ethyl acetate, to afford the product as a light brown oil (9.5 g). $^1$H NMR (360 MHz, CDCl$_3$) δ$_H$1.9–2.03 (2H, m, NCH$_2$CH$_2$), 2.07–2.19 (2H, m, NCH$_2$CH$_2$), 2.27 (3H, s, NC H$_3$), 2.51–2.62 (2H, m, NCH$_2$), 2.72–2.86 (2H, m, NC H$_2$), 3.65 (3H, s, OOCH$_3$), 6.98–7.06 (2H, m, ArH), 7.27–7.39 (2H, m, ArH). MS CI$^+$m/z 224 (M+1$^+$, 100%).

c) The ester (7.13 g) was dissolved in anhydrous THF (40 ml) and stirred under nitrogen. Lithium aluminium hydride (1.0M in tetrahydrofuran 14.2 ml) was added and the reaction was left stirring at room temperature for 1 hour. Water (0.54 ml) followed by 15% NaOH (0.54 ml) and finally more water (1.6 ml) were added. The reaction was diluted down with tetrahydrofuran and filtered through celite. The solvent was removed to afford a white solid (5.94 g). $^1$H NMR (360 MHz, CDCl$_3$) δ$_H$ 1.84–1.95 (2H, m, NCH$_2$CH$_2$), 2.12–2.24 (7H, m, CH$_3$+NCH$_2$CH$_2$), 2.51–2.59 (2H, m, NCH$_2$), 3.55 (2H, s, CH$_2$O), 7.02–7.09 (2H, m, ArH), 7.23–7.34 (2H, m, ArH). MS CI$^+$m/z 224 (M+1$^+$, 100% ).

d) The alcohol (4.1 g) was dissolved in anhydrous dimethyl formamide (60 ml), sodium hydride (0.61 g) was added portionwise and the reaction sonicated for 30 minutes. The 3,5-bis(trifluoromethyl) benzyl bromide (3.5 ml) was added, the colour changed from light brown to almost black and back to light brown, heat was evolved. The reaction was left for 3 hrs. The reaction mixture was dispersed between water/ethyl acetate. The aqueous layer was extracted with ethyl acetate (2×50 ml). The combined organics were washed with brine, dried (MgSO$_4$) and concentrated to afford a brown oil. Purification was carried out on flash silica elution 1% methanol in dichloromethane →6% methanol in dichloromethane which afforded a light brown oil (4.2 g). $^1$H NMR (360 MHz, CDCl$_3$) δ$_H$ 1.98–2.12 (2H, m, NCH$_2$C H$_2$), 2.18–2.35 (7H, m, CH$_3$+NCH$_2$CH$_2$), 2.58–2.76 (2H, m, NCH$_2$), 3.44 (2H, s, CH$_2$O), 4.44 (2H, s, CH$_2$OCH$_2$Ar), 7.00–7.08 (2H, m, ArH), 7.53 (2H, s, ortho H), 7.74 (1H, s, para H). MS CI$^+$m/z 450 (M$^+$+1, 100%)

e) The alkylated product (4.18 g) was dissolved in 1,2 dichloroethane (40 ml) under nitrogen, vinyl chloroformate (2.4 ml) was added and the reaction was heated at reflux for 18 hrs. An extra portion of vinyl chloroformate (1 ml) was added and a further 2 hrs of heating at reflux was required for complete reaction. The 1,2 dichloroethane was removed by rotary evaporator. Purification was carried out on flash silica elution 100%. Dichloromethane to afford a light brown oil (3.1 g). $^1$H NMR (360 MHz, CDCl$_3$) δ$_H$ 1.85–1.93 (2H, m, NCH$_2$CH$_2$), 2.22–2.31 (2H, m, NCH$_2$CH$_2$), 3.43 (2H, s, OCH$_2$C), 3.86–3.92 (2H, m, NCH$_2$), 4.42–4.50 (3H, m, OC H$_2$Ar+=CHH), 4.74–4.79 (1H, dd,=CHH), 7.03–7.11 (2H, m, ortho H[fluorine ring]), 7.17–7.23 (1H, m, —C H═CH$_2$), 7.29–7.36 (2H, m, meta ArH), 7.53 (2H, s, ortho CF$_3$H), 7.75 (1H, s, para H's). MS CI$^+$m/z 506 (M+1$^+$%) 523 (M+(NH$_4$)$^+$, 70%).

f) The vinyl oxycarbonyl group was removed by stirring in methanolic hydrogen chloride solution for 3 hrs. When the reaction is complete by TLC the methanol is removed in vacuo to afford the hydrochloride salt as a white solid. Without further purification the hydrochloride salt (1.8 g) was dissolved in dimethylformamide (15 ml) under nitrogen, an excess of potassium carbonate (2.63 g) and the N-t-butoxychloromethylimidiazone (0.95 g) were added and stirred at room temperature overnight. When no starting material remained by TLC (10% MeOH in DCM), the reaction mixture was dispersed between water and ethyl acetate. The aqueous layer was extracted with ethyl acetate (2×30 ml). The combined organics were washed with brine, dried (MgSO$_4$) and concentrated to afford a brown oil. The recovered oil was dissolved in toluene with a catalytic amount of potassium t-butoxide and heated at 80° C. for 3 hrs. Purification was carried out on flash silica eluted with 4% MeOH in DCM rising to 8% MeOH in DCM. Further purification on Lobar column elution with 5% MeOH in DCM to afford a white solid (0.65 g). Recrystallisation was carried out from diethyl ether/hexane. $^1$H NMR (360 MHz, CDCl$_3$) $\delta_H$ 1.95–206 (2H, m, NCH$_2$CH$_2$), 2.19–2.39 (4H, m, NCH$_2$CH$_2$), 2.62–2.72 (2H, m, NCH$_2$), 3.35 (2H, s, NC H$_2$het), 3.44 (2H, s, C CH$_2$O), 4.43 (2H, s OCH$_2$Ar), 7.00–7.07 (2H, t, J$_1$=8.6 Hz, J$_2$=8.7 Hz, meta H), 7.26–7.32 (2H, dd, J=8.8 Hz, J=5.2 Hz, ortho H's), 7.51 (2H, s, ortho H), 7.73 (1H, s, para H). MS CI$^+$m/z 533 (M$^+$+1, 100%). C$_{24}$H$_{23}$N$_4$O$_2$F$_7$ requires C, 54.14; H, 4.35; N, 0.52 found C, 54.16; H, 4.20; N, 10.23.

EXAMPLE 15

5-[4-(3,5-Bistrifluoromethylbenzyloxymethyl)-4-(2-fluorophenyl)-piperidin-1-ylmethyl]-2,4-dihydro-[1,2,4]-triazol-3-one Prepared analogously to Example 14. Mp 107°–110° C. $^1$H NMR (360 MHz, CDCl$_3$) $\delta_H$10.4(–1H, bs, NH), 7.71 (1H, s, 4'-H Ar'), 7.47 (2H, s, 2'-H and 6'-H Ar'), 7.21–7.31 (2H, m, 4-H and 6-H Ar), 7.12 (1H, t, J=6.9 Hz, 5-H Ar), 6.90 (1H, dd, J$_{H-F}$=13.3, J$_{H-H}$=8.1 Hz, 3-H Ar), 4.45 (2H, s, OCH$_2$Ar'), 3.68 (2H, s, CH$_2$O), 3.35 (2H, s, NCH$_2$), 2.6–2.7 (2H, bm), 2.3–2.5 (4H, bm) and 1.95–2.05 (2H, bm, (CH$_2$CH$_2$)$_2$N). m/z (CI$^+$) 533 (M+1, 100%); (CI$^-$) 531 (M-1, 8). Found C, 53.51; H, 4.22; N, 10.02. C$_{24}$H$_{23}$F$_7$N$_4$O$_2$· 0.4H$_2$O requires C, 53.42; H, 4.45; N, 10.38.

EXAMPLE 16

5-[4-(3,5-Bistrifluoromethylbenzyloxymethyl)-4-(3-fluorophenyl)piperidin-1-ylmethyl]-2,4-dihydro-[1,2,4]-triazol-3-one Prepared analogously to Example 14. $^1$H NMR (360 MHz, CDCl$_3$) $\delta_H$ 1.96–2.02 (2H, m, NCH$_2$CH$_2$), 2.20–2.24 (2H, m, NCH$_2$CH$_2$), 2.30–2.38 (2H, m, NCH$_2$), 2.64–2.70 (2H, m, NCH$_2$), 3.34 (2H, s, NCH$_2$ het), 3.46 (2H, s, CC H$_2$O), 4.44 (2H, s, OCH$_2$Ar), 6.92–6.97 (H, m, ArH), 7.03–7.06 (1H, m, ArH), 7.10–7.19 (1H, m, ArH), 7.28–7.34 (H, m, ArH), 7.61 (2H, s, ArH), 7.73 (1H, s, ArH), 10.14 (1H, bs, NH). MS CI$^+$m/z 533 (M+1$^+$, 40%). mp 107°–108° C.

EXAMPLE 17

3-Phenyl-3-(3,5-bistrifluromethyl)benzyloxymethyl piperidine tosylate a) 4-Phenyl, 4,4-diethoxycarbonyl butyronitrile Acrylonitrile (33.0 g) was added dropwise to a stirred solution of diethyl phenylmalonate (70.8 g) in dry t-Butanol (80 ml). After the addition of approximately 20 drops, a solution of 30% methanolic potassium hydroxide (1.0 ml) was added. Once the addition of acrylonitrile was complete, further 30% methanolic potassium hydroxide (1.0 ml) was added and the reaction warmed to 50° C. for one hour. The reaction mixture was allowed to cool to room temperature, then diluted with water (250 ml) and extracted into ether. The organic extract was dried (MgSO$_4$), filtered, and the solvent removed under reduced pressure. The recovered product was purified by distillation (75 g). bp 159°–162° C. @ 1.2 mmHg. $^1$H NMR (360 MHz, CDCl$_3$) $\delta_H$ 1.26 (6H, t, J=7.5 Hz, 2×CH$_2$CH$_3$), 2.34 (2H, t, J=4.0 Hz, CH$_2$CH$_2$CH), 2.62 (2H, t, J=4.0 Hz, CH$_2$CH$_2$CH), 4.26 (4H, m, 2×CH$_2$CH$_3$), 7.34 (5H, m, Ar H); m/z (CI$^+$) 307 (M+NH$_4^+$)$^+$.

b) 3-Phenyl-3-ethoxycarbonyl piperidine 2-one

A solution of 4-phenyl 4,4 diethoxycarbonyl butyronitrile (16.49 g) in dry ethanol (250 ml) was hydrogenated over platinum dioxide at 50 psi for 8 hours. The catalyst was filtered off and the solvent removed under reduced pressure. Product recrystallised from ether (14.1 g) mp 79°–80° C. $^1$H NMR (360 MHz, CDCl$_3$) $\delta_H$1.24 (t, 3H, J=7.0 Hz, CH$_2$ CH$_3$), 1.71 (2H, m, CH$_2$CH$_2$CH$_2$C), 2.32 (1H, m, CH$_2$CH$_2$CHH), 2.68 (1H, m, CH$_2$CH$_2$CHH), 3.36 (2H, m, CH$_2$CH$_2$CH$_2$C), 4.22 (2H, q, J=7.0 Hz, CH$_2$CH$_3$), 6.26 (1H, bs, NH), 7.30 (5H, m, Ar H). m/z (CI$^+$) 248 (M+1)$^+$.

c) (I) N-t-Butoxycarbonyl-3-phenyl-3-hydroxymethyl piperidine

3-Phenyl-3-ethoxycarbonyl piperidine 2-one (7.0 g) was added portionwise to a stirred solution of lithium aluminium hydride (2.15 g) in dry tetrahydrofuran (100 ml). Once addition was complete the solution was warmed to reflux for two hours. The reaction was then cooled to room temperature, and water (3 ml) and 1N sodium hydroxide solution (3 ml) added, followed by t-butoxycarbonyl anhydride (6.17 g) and dry dichloromethane (60 ml). The resulting mixture was stirred at room temperature for 18 hours. The white precipitate was filtered off and the filtrate extracted into dichloromethane (250 ml). The organic layers were dried (MgSO$_4$), filtered and the solvent removed under reduced pressure. Product recrystallised from EtOAc/nHex (13.1 g). mp 101°–104° C. $^1$H NMR (360 MHz, CDCl$_3$) $\delta_H$1.46 (9H, s, C(CH$_3$)$_3$), 2.00–4.00 (CH$_2$ envelope), 7.35 (5H, m, ArH); m/z (CI$^+$), 291 (M+1)$^+$.

d) (±) 3-Phenyl-3-(3,5-bistrifluoromethyl)benzyloxymethyl piperidine tosylate

KHMDS (21 ml×0.5 mol) was added to a stirred solution of (±) N-$^t$butoxycarbonyl-3-phenyl-3-hydroxymethyl piperidine (279 mg) in dry tetrahydrofuran (10 ml) at –78° C. The solution was warmed to room temperature over 30 min and then re-cooled to –78° C. 3,5-Bis(trifluoromethyl) benzyl bromide (179 μl) was then added and the solution allowed to warm to room temperature over 18 hours. The reaction mixture was poured into water (50 ml), and extracted into ethyl acetate (50 ml). The organic extract was stirred over magnesium sulphate, filtered, and the solvent removed under reduced pressure, to afford a yellow oil. Chromatography on SiO$_2$ (20%, EtOAc/nHex) afforded a clear oil. Treatment of the recovered oil with a saturated solution of hydrogen chloride in ether afforded removal of the protecting group. The recovered salt was taken up in water (20 ml), basified with 4N sodium hydroxide solution, and extracted into ethyl acetate (50 ml). The organic layer was dried (MgSO$_4$), filtered, and the solvent removed under reduced pressure to afford a clear off. The recovered product was treated with p-toluene sulphonic acid to afford the tosylate salt (189 mg) mp 179°–180° C. $^1$H NMR (360 MHz, DMSO-D$_6$) $\delta_H$[Tosyl signals omitted for clarity] 1.63 (1H, m, CH$_2$CH$_2$CHH), 1.74 (1H, m, CH$_2$CH$_2$CHH), 1.96 (1H, m, CH$_2$CHHCH$_2$), 2.02 (1H, m, CH$_2$CHHCH$_2$), 3.00 (2H, m, CH$_2$CH$_2$CH$_2$), 3.52 (1H, d, J=10.0 Hz, NCHH—C), 3.55 (1H, d, J=6.0 Hz, CCHH—OCH$_2$Ar), 3.62 (1H, d, J=6.0 Hz, CCHH—OCH$_2$Ar), 3.65 (1H, d, J=10.0 Hz, NCHH—C), 4.53 (1H, d, J=8.0 Hz, OCHHAr), 4.60 (1H, d, J=8.0 Hz, OC HHAr), 7.32 (5H, m ArH), 7.48 (2H, s, C—C H—CCF₃×2), 7.77 (1H, s, CF₃C—CH—CCF₃). m/z (CI⁺) 418 (M+1)⁺. $C_{28}H_{29}NO_4SF_6$ requires C, 57.04; H, 4.95; N, 2.37. Found C, 56.86; H, 4.65; N, 2.26%.

EXAMPLE 18

4-Phenyl-{4-[1-(3,5-(Bistrifluoromethyl)phenyl]ethoxymethyl} piperidine hydrochloride

METHOD A a) 1-(3,5-Bistrifluoromethyl)phenyl-1-ethanol

Sodium borohydride (2.2 g) was added to a stirred solution of 3,5-bistrifluoromethyl acetophenone (15.0 g) in dry methanol (100 ml). The resulting solution was stirred for 1 hour at room temperature, and then reduced to dryness under reduced pressure. The solid residue was partitioned between saturated ammonium chloride solution and ethyl acetate. The organic layer was separated and dried (MgSO₄), filtered, and the solvent removed under reduced pressure. Recovered product was recrystallised from pentane (12.6 g) mp 71°–72° C. ¹H NMR (360 MHz, CDCl₃) δ1.56 (3H, d, J=7.0 Hz, CH—CH₃), 2.00 (1H, bs, OH), 5.05 (1H, q, J=7.0 Hz, CH—CH₃), 7.8 (1H, CF₃C—CH—CCF₃), 7.89 (2H, C—CH—CCF₃×2).

b) 1-[3,5-(Bistrifluoromethyl)phenyl]-1-bromoethane 1-(3,5-Bistrifluoromethyl)phenyl-1-ethanol (10 g) was treated with phosphorous tribromide (3.75 ml). After 1 hour the mixture was added to water and extracted with hexane. The organic solution was dried (Na₂SO₄) and filtered through silica gel to give, after evaporation of the solvent in vacuo, the title compound as a colourless liquid. ¹H NMR (360 MHz, CDCl₃) δ2.08 (3H, d, J=7 Hz), 5.21 (1H, q, J=7 Hz), 7.80 (1H, s) and 7.87 (2H, s).

c) 4-Phenyl-4-[1-(3,5-(bistrifluoromethyl)phenyl)ethoxymethyl]piperidine

The title compound was prepared by the method of Examples 1 and 2 using 1-(3,5-bistrifluoromethyl)phenyl)-1-bromoethane. Mpt 86°–89° C. ¹H NMR (360 MHz, DMSO-d₆) δ1.29 (1H, d, J=6.4 Hz), 2.05 (2H, m), 2.31 (2H, m), 2.71 (2H, m), 3.17 (2H, m), 3.21 (1H, d, J=9.2 Hz), 3.45 (1H, d, J=9.2 Hz), 4.56 (1H, q, J=6.4 Hz), 7.27 (1H, m), 7.38 (4H, m), 7.72 (2H, s) and 7.96 (1H, s). m/z (CI⁺)(M⁺+1). $C_{22}H_{23}F_6NO$. HCl 0.25H₂O requires C, 55.94; H, 5.23; N, 2.96. Found C, 55.89; H, 5.27; N, 3.10.

METHOD B a) 1-'Butoxycarbonyl-4-phenyl-4-[3,5-bistrifluoromethylbenzoyloxymethyl]piperidine 1-(3-Dimethylaminopropyl)-3-ethyl-carbodiimide hydrochloride (897 mg) was added to a stirred solution of 3,5-bistrifluoromethyl benzoic acid (292 mg) and 4-dimethylamine pyridine (483 mg) in dry DMF (20 ml). The resulting solution was stirred for 30 rain at room temperature at which time the compound of Example 1 part a) (1.0 g) was added. The resulting solution was stirred at room temperature for 19 hrs. At this time the reaction was diluted with water (200 ml) and extracted into ethyl acetate. The organic layers were separated, washed with water, brine, and dried over MgSO₄. Filtration and removal of solvent under reduced pressure afforded a yellow oil. Purification by MPLC (20% EtOAc/ nHexane) afforded the product as a clear oil. ¹H NMR (360 MHz, CDCl₃) δ1.4 (9H, s, N—CO—CCCH₃), 1.95 (2H, m, NCH₂—CHH×2), 2.3 (2H, m, NCH₂—CHH×2), 3.03 (2H, m, NCHH—CH₂×2). 3.8 (2H, m, NCHH—CH₂×2), 4.35 (2H, s, CH₂O—CO), 7.0–7.2 (5H, m, ArH), 8.01 (1H, s, CF₃C—CH—CCF₃), 8.25 (2H, s, C—CH—CCF₃×2).

b) 1-'Butoxycarbonyl-4-phenyl-4-[1-(3,5-bistrifluoromethylphenyl]piperidine

TiCl₄ (1.06 g) was added to cooled (0° C.) stirred THF under a dry N₂ atmosphere. After the exotherm had subsided the solution was allowed to warm to room temperature and THEDA (1.69 g) added followed 15 rain later by freshly activated Zn dust (819 mg). The resulting mixture was stirred for 30 min at room temperature at which point CH₂Br₂ (216 µl) and the compound of part a (716 mg) were added. The reaction was allowed to proceed for 18 hrs at room temperature. After this time the reaction was quenched with saturated K₂CO₃ (7 ml) and diluted with Et₂O. The resulting black suspension was filtered through a plug of GIII Al₂O₃, eluting with 1% Et₃N/Et₂O. The filtrate was dried over MgSO₄, filtered and the solvent removed under reduced pressure. The residual oil was purified by MPLC (10% EtOAc/nHex)to afford the product (290 mg). ¹H NMR (360 MHz, CDCl₃) δ1.2 (9H, s, C(CH₃)₃), 1.95 (2H, m, NCH₂—CHH×2), 2.38 (2H, m, NCH₂CHH×2), 3.05 (2H, m, NCHH—CH₂×2), 3.8 (2H, s, CH₂O-), 3.95 (2H, m, NC HH—CH₂×2), 4.21 (1H, d, J=1.0 Hz, C=CHH), 4.63 (1H, d, J=1.0 Hz, C=CHH), 7.1–7.3 (5H, m, ArH), 7.7 (1H, s, CF₃—C—CH—CCF₃), 7.76 (2H, s, C—CH—CCF₃×2).

c) 4-Phenyl-4-1-(3,5-(bistrifluoromethyl)phenyl)ethoxymethyl]piperidine

The product of part (b) (290 mg) was hydrogenated over 5% RH/Al₂O₃ in ethyl acetate for 30 min at atmospheric pressure. The catalyst was filtered off and solvent removed. The residual oil was purified by MPLC (5% EtOAc/nHexane) followed by treatment with ether/HCl to afford the title compound. Identical in all respects to that of Example 18, Method A, part (c).

EXAMPLE 19

1-Methyl-4-phenyl-4-[3,5(bistrifluoromethyl)benzyloxymethyl]piperidine tosylate

Sodium cyanoborohydride (147 mg) was added to a stirred suspension of the compound of Example 2 (533 mg) and formaldehyde (175 mg, 0.5 ml×37%) in dry methanol containing acetic acid (1.0 ml). The resulting solution was stirred for 18 hours at room temperature. After this time the solvent was removed under reduced pressure and the residual oil taken up in water and basified to pH 10. The aqueous solution was extracted into ethyl acetate, separated and dried (MgSO₄). Filtration and removal of solvent gave a yellow oil. Chromatography on silica gel (5% MeOH/ CH₂Cl₂) afforded a clear oil (473 mg). The recovered oil was treated with a solution of p-toluene sulphonic acid monohydrate (207 mg) to afford the salt. Recrystallisation from ethyl acetate gave the title compound as a white powder (580 mg). mp 89°–91° C. ¹H NMR (360 MHz, DMSO₆) δ2.01 (2H, m, NCH₂CH₂), 2.55 (2H, m, NCH₂CH₂), 2.67 (3H, s, NCH₃), 2.67 (3H, s, NCH₃), 2.71 (2H, m, NCH₂CH₂), 3.37 (2H, s, CH₂OCH₂Ar), 4.56 (2H, s, CH₂OCH₂Ar), 7.30–7.48 (5H, m, ArH), 7.70 (2H, s, C—CH—CCF₃×2), 7.99 (1H, s, CF₃C—CH—CCF₃); MS CI⁺432 (M+1)⁺.

The following compounds were prepared analogously.

EXAMPLE 20

1-Isopropyl-4-phenyl-4-[3.5(bistrifluoromethyl)benzyloxymethyl]piperidine tosylate mp 158°–60° C. ¹H NMR (DMSO-d₆) 1.09 (6H, d, J=11.0 HZ, (CH₃)₂CH), 2.01 (2H, m, NCH₂CH₂), 2.51 (2H, m, NC H₂CH₂), 3.19 (1H, sept, J=11.0 Hz, (CH₃)₂CH), 3.37 (2H, s, CHhd 2OCH₂Ar), 4.57 (2H, s, CH₂OCH₂Ar), 7.36–7.45 (5H, m, ArH), 7.73 (2H, s, C—CH—CCF₃×2), 8.00 (1H, s, CF₃C—CH—CCF₃); MS CI⁺ 460 (M+1)⁺; $C_{31}H_{35}NO_4SF_6$ requires C, 58.95; H, 5.59; N, 2.22. Found C, 59.02; H, 5.66; N, 2.26%.

EXAMPLE 21

1-(2-Phenyl)ethyl-4-phenyl-4-[(3,5(bistrifluoromethyl)benzyloxymethyl]piperidine tosylate mp 166°–167° C. $^1$H NMR (360 MHz, CDCl$_3$ free base) δ2.10 (2H, m, NCH$_2$CH$_2$), 2.41 (4H, m, NCH$_2$CH$_2$ and Ph—CH$_2$CH$_2$), 2.55 (2H, m, NCH$_2$CH$_2$), 2.93 (4H, m, PhCH$_2$CH$_2$), 3.51 (2H, s, CH$_2$OCH$_2$Ar), 4.42 (2H, s, CH$_2$OCH$_2$Ar), 7.00–7.40 (10H, m, ArH), 7.49 (2H, s, C—C H—CCF$_3$); MS Cl$^+$ 522 (M+1)$^+$; C$_{36}$H$_{37}$NO$_4$SF$_6$·½H$_2$O. Requires C, 61.53; H, 5.45; N, 1.99; Found C, 61.92; H, 5.30; N, 1.99%.

EXAMPLE 22

1-Isobutyryl-4-phenyl-4-[(3,5-bistrifluoromethyl)benzyloxymethyl]piperidine tosylate mp 159°–62° C. $^1$H NMR (360 MHz, DMSO d$_6$) 0.95 (6H, d, J=11.0 Hz, (CH$_3$)$_2$), 2.2–2.5 (4H, brm, NCH$_2$C H$_2$×2), 2.6 (2H, m, NCH$_2$CH$_2$), 2.8 (2H, d, J=7.0 Hz, N—C H$_2$—CH), 3.31 (1H, brm, CH(CH$_3$)$_2$), 3.39 (2H, s, C H$_2$OCH$_2$Ar), 3.42 (2H, m, NCH$_2$(H$_2$)), 4.57 (2H, s, CH$_2$OC H$_2$Ar), 7.31–7.45 (5H, m, ArH), 7.72 (2H, s, C—C H—CCF$_3$×2), 7.99 (1H, s, CF$_3$C—CH—CCF$_3$); MS Cl$^+$ 474 (M+1)$^+$; C$_{32}$H$_{37}$NO$_4$SF$_6$·H$_2$O requires C, 57.90; H, 5.92; N, 2.11; Found C, 57.62; H, 5.74; N, 1.83%.

EXAMPLE 23

1-Isovaleryl-4-phenyl-4-[(3,5-bistrifluoromethyl)benzyloxymethyl]piperidine tosylate mp 141°–142° C. $^1$H NMR (360 MHz, DMSO d$_6$) 0.64 (9H, s, (CCH$_3$)$_3$), 1.49 (3H, m, NCH$_2$—CHH and (CH$_3$)$_3$C—CH$_2$), 2.02 (3H, m, NCH$_2$—CHH and ((CH$_3$)$_3$C—CH$_2$CH$_2$), 2.49 (2H, m, NCH$_2$CH$_2$), 2.59 (2H, m, NCH$_2$), 3.36 (2H, s, CH$_2$OCH$_2$Ar), 4.57 (2H, s, CH$_2$OC H$_2$Ar), 7.36–7.42 (5H, m, ArH), 7.72 (2H, s, C—C H—CCF$_3$×2), 7.99 (1H, s, CF$_3$C—CH—CCF$_3$); MS Cl$^+$ 502 (M+1)$^+$; C$_{34}$H$_{41}$NO$_4$SF$_6$ requires C, 60.61; H, 6.13; N, 2.48; Found C, 60.41; H, 5.84; N, 2.01%.

EXAMPLE 24

(±)-5-{4-[1-(3,5-Bistrifluoromethylphenyl)ethoxymethyl]-4-phenyl-piperidine-1-yl}-2,4-dihydro-[1,2,4]-triazol-3-one Prepared from the compound of Example 18 by the method of Example 12; mp 86°–88° C. $^1$H NMR (360 MHz, CDCl$_3$) δ1.35 (3H, d, J=6.5 Hz), 2.00–2.16 (2H, m), 2.21–2.46 (4H, m), 2.67–2.78 (2H, m), 3.27 (1H, d, J=9 Hz), 3.37 (1H, d, J=9 Hz), 3.39 (2H, s), 4.30 (1H, q, J=6.5 Hz), 7.26–7.39 (5H, m), 7.52 (2H, s), 7.76 (1H, s); m/e Cl$^+$ 529 (M+1). Found: C, 57.15; H, 4.99; N, 10.51%. C$_{25}$H$_{26}$F$_6$N$_4$O$_2$ requires C, 56.82; H, 4.96; N, 10.60.

EXAMPLE 25

4-Phenyl-4-[(3-chloro-5-methyl)benzyloxymethyl]piperidine hydrochloride

Prepared following the procedure of Examples 1 and 2; mp 159°–160° C. C$_{20}$H$_{24}$NOCl. HCl requires C, 65.57; H, 6.88; N, 3.82; Found C, 65.69; H, 6.91; N, 3.60%.

EXAMPLE 26

4-Phenyl-4-[(3-bromo-5-methyl)benzyloxymethyl]piperidine hydrochloride

Prepared following the procedures of Examples 1 and 2; mp 55°–57° C. C$_{20}$H$_{24}$NOBr. HCl·0.4H$_2$O requires C, 57.47; H, 6.22; N, 3.35; Found C, 57.36; H, 6.10; N, 3.09%.

4-Phenyl-4-[(3-methyl-5-t-butyl)benzyloxymethyl]piperidine hydrochloride

Prepared following the procedures of Examples 1 and 2; mp 51°–52° C. C$_{24}$H$_{33}$NO. HCl. H$_2$O requires C, 71.00; H, 8.94; N, 3.45; Found C, 71.22; H, 9.16; N, 3.48%.

EXAMPLE 28

Methyl-2-[4-phenyl-4-(3,5-bistrifluoromethyl benzyloxymethyl) piperidine]acetate hydrochloride Potassium carbonate (3 mg) was added to a stirred solution of the compound of Example 2 (4.47 g) and methyl bromoacetate (1.5 g)in dry dimethyl formamide (25 ml). Stirred at room temperature for 18 hours. After this time the reaction was poured into water (100 ml), extracted into ethyl acetate (50 ml), dried (MgSO$_4$), filtered and the solvent removed under reduced pressure. Purification by flash chromatography (SiO$_2$ 30% EtOAc/nHg) followed by treatment with ethereal HCl afforded the product as a white powder (2.23 g), mp 63°–65° C. C$_{24}$H$_{25}$NO$_3$F$_6$. HCl. ½H$_2$O requires C, 53.90; H, 5.10; N, 2.62; Found C, 54.01; H, 5.24; N, 2.74%.

EXAMPLE 29

N-methyl-4-phenyl-4-[3,5-bistrifluoromethylbenzyloxymethyl]piperidine methiodide Excess methyl iodide was added to a solution of the compound of Example 19 (80 mg) in dry acetone. The solution was warmed to reflux for 4 hours, cooled to room temperature and the solvent removed under reduced pressure. Product recrystallised from isopropanol (109 mg), mp 197°–199° C. C$_{23}$H$_{24}$NOF$_6$I. H$_2$O requires C, 46.71; H, 4.77; N, 2.37; Found C, 46.64; H, 4.37; N, 2.31%.

EXAMPLE 30

4-[(3,5-Bistrifluoromethyl)benzyloxymethyl]-4-phenyl-1-(4H-[1,2,4]triazol-3-yl-methyl)piperidine dihydrochloride Potassium carbonate (608 mg) was added to a suspension of the compound of Example 2 (500 mg) and N-formamido-2-chloromethyl acetamidine (382 mg) in dry dimethyl formamide. The solution was warmed to 60° C. for 2 hours and then to 140° C. for a further 1 hour. The reaction was cooled to room temperature, diluted with water and extracted into ethyl acetate. The organic layers were separated, washed with water, then brine, and dried (MgSO$_4$). Filtration and removal of solvent afforded a yellow oil. Purification by flash chromatography (SiO$_2$ 10%, MeOH/DCM) followed by treatment with ethereal hydrogen chloride afforded the product as a white powder (200 mg), mp 119°–120° C. C$_{24}$H$_{24}$N$_4$OF$_6$. 2HCl requires C, 50.44; H, 4.59; N, 9.81. Found C, 50.40; H, 4.62; N, 10.10%.

EXAMPLE 31

5-[4-(3-Methyl-5-t-butyl)benzyloxymethyl]4-phenyl-piperidin-1-ylmethyl]2,4-dihydro-[1,2,4]-triazol-3-one Prepared analogously to Example 12 from the compound of Example 27; mp 144°–145° C. MS Cl$^+$ 448 (M+1)$^+$.

EXAMPLE 32

2-[4-Phenyl-4-[3,5(bistrifluoromethyl)benzyloxymethyl]-N-3-pyridyl methyl-N-methyl acetamide. Dihydrochloride Prepared analogously to Example 28; mp 135°–137° C. $C_{30}H_{31}N_3O_2F_6 \cdot 2HCl \cdot 2H_2O$ requires C, 52.48; H, 5.14; N, 6.12; Found C, 52.12; H, 5.29; N, 6.22%.

EXAMPLE 33

4-[(3,5-Bistrifluoromethyl)benzyloxymethyl]-1-(2-methylthiazol-5-yl-methyl)-4-phenyl piperidine dihydrochloride Prepared analogously to Example 28; mp 110°–113° C. $C_{26}H_{26}N_2OSF_6 \cdot 2HCl$ requires C, 51.92; H, 4.89; N, 4.66; Found C, 51.72; H, 4.64; N, 4.56%.

EXAMPLE 34

4-[(3,5-Bistrifluoromethyl)benzyloxymethyl]-1-[1,2,4]-oxadiazol-3-ylmethyl-4-phenyl piperidine hydrochloride Prepared analogously to Example 28; mp 90°–91° C. $C_{24}H_{23}N_3O_2F6 \cdot HCl$ requires C, 53.79, H, 4.51; N, 7.84; Found C, 53.77; H, 4.52; N, 7.53%.

EXAMPLE 35

$(\pm)_s$-[4-(3,5-bistrifluoromethylbenzyloxymethyl)-4-phenyl-piperidin-yl)-1-ethyl]-2,4-dihydro-[1,2,4]-triazol-3-one tosylate Prepared analogously to Example 12; mp 230°–231° C. $C_{32}H_{34}N_4O_5SF_6 \cdot \frac{1}{2}H_2O$ requires C, 54.16; H, 4.97; N, 7.89; Found C, 54.12; H, 4.74; N, 7.99%.

EXAMPLE 36

1-[4-(3,5-Bistrifluoromethyl)-benzyloxymethyl-4-phenyl-piperidin-1-yl]-2-pyrrolidin-1-yl-acetamide Prepared analogously to Example 10, mp 180°–182° C. $C_{34}H_{36}N_2SO_5F_6$ requires C, 58.28; H, 5.47; N, 3.99; Found C, 58.45; H, 5.60; N, 3.92%.

EXAMPLE 37

N-methanesulphonyl-2-[4-phenyl-4-(3,5-bistrifluromethylbenzyloxymethyl)piperidin-1-yl]acetamide (a) N-Bromoacetylmethanesulfonamide Sodium hydride (1.68 g×60% ) was added to a stirred solution of methanesulfonamide (2.0 g) in dry tetrahydrofuran (20 ml) at room temperature. The resulting solution was stirred at room temperature for 1 hour, as which time it was treated with a solution of bromoacetyl bromide (4.2 g) in dry tetrahydrofuran (10 ml). After 1 hour the solvent was removed under reduced pressure and the residue taken up in water and acidified to pH3. The acidic solution was extracted into ethyl acetate, dried (MgSO$_4$), filtered and the solvent removed under reduced pressure. Recrystallisation from isopropanol afforded the product as white needles: mp 112°–114° C.

(b) N-methanesulphonyl-2-[4-phenyl-4-(3,5-bistrifluoromethyl)benzyloxymethyl) piperidin-1-yl]acetamide Prepared analogously to Example 28 from the product of part (a) and the compound of Example 2; mp 97°–99° C. $C_{24}H_{26}H_2SO_4F_6 \cdot \frac{1}{2}H_2O$ requires C, 51.33; H, 4.84; N, 4.99; Found C, 51.47; H, 4.83; N, 5.01.

EXAMPLE 38

N-phenylsulphonyl-2-[4-phenyl-4-(3,5-bistrifluoromethylbenzyloxymethyl)piperidin-1-yl acetamide (a) N-Bromoacetylphenylsulfonamide Prepared analogously to the compound of Example 36, part (2).

(b) N-phenylsulphonyl-2-[4-phenyl-4-(3,5-bistrifluoromethylbenzyloxymethyl)piperidin-1-yl]acetamide Prepared analogously to Example 37 from the product of part (a) and the compound of Example 2; mp 110°–114° C. MS CI$^+$ 614 (M+1)$^+$.

EXAMPLE 39

4-Phenyl-4-[(3-phenyl)benzyloxymethyl]piperidine hydrochloride

Prepared following the method of Examples 1 and 2. The crude concentrate was crystallised from hot ethyl acetate to yield the title compound as a white crystalline solid (2.60 g); m.p. 158.5°–159.0° C (EtOAc). $^1$H NMR (360 MHz, d$_6$-DMSO) 9.00 (2H, bs, $^+$NH$_2$), 7.35–7.60 (12H, m), 7.26 (1H, t, J=7.2) and 7.16 (1H, d, J=7.6, Ar—H), 4.46 (2H, s, OC$\underline{H}_2$Ar), 3.46 (2H, s, C.CH$_2$O), 3.16 (2H, m, 2×C $\underline{H}H$.CH$_2$N), 2.71 (2H, t, J=10.5, 2×CH$\underline{H}$.CH$_2$N), 2.34 (2H, bm) and 2.13 (2H, m, CH$_2$NCH$_2$). m/z (CI$^+$) 358 (M+1, 100%). Found C, 76.51; H, 7.44; N,3.70. $C_{25}H_{27}NO \cdot HCl$ requires C, 76.21; H, 6.92; N, 3,56%. HPLC>99.5%.

EXAMPLE 40

5-[4-(3-Phenyl)benzyloxymethyl]-4-phenyl-piperidin-1-yl-methyl-2,4-dihydro-[1,2,4]-triazol-3-one Prepared from the compound of Example 39 (2.0 g) as described in Example 12. Flash silica gel chromatography eluting with 9:1 dichloromethane:methanol (Rf=0.21) gave a yellow gloss (1.8 g). Crystallisation from ethyl acetate and diethyl ether gave the title compound as solids (1.56 g); m.p. 148°–149° C. (EtOAc-Et$_2$O). $^1$H NMR (360 MHz, d$_6$-DMSO) 11.21 (1H, bs) and 11.16 (1H, s, 2×NH), 7.29–7.59 (12H, m), 7.19 (1H, t, J=7.2) and 7.12 (1H, d, J=7.6, Ar—H), 4.41 (2H, s, OC$\underline{H}_2$Ar), 3.43 (2H, s, C.CH$_2$O), 3.15 (2H,s, NCH$_2$. C=N), 2.55 (2H, bm, 2×C $\underline{H}H$.CH$_2$N), 2.15 (4H, bm) and 1.93 (2H, m, 2×CH$\underline{H}$.C H$_2$N). m/z (CI$^+$) 455 (M+1, 100%). Found C, 74.02; H, 6.61; N, 12.47. $C_{28}H_{30}N_4O_2$ requires C, 73.97; H, 6.66; N, 12.32%. HPLC>99.5%.

EXAMPLE 41

5-[(4-Benzyloxymethy)-4-phenyl-piperidin-1-ylmethyl]-2,4-dihydro-[1,2,4]-triazol-3-one hydrochloride Prepared from the compound of Example 5 by the method of Example 12; m.p. 144°–147° C. $C_{22}H_{26}N_4O_2 \cdot HCl$ requires C, 69.82; H, 6.93; N, 14.80; Found C, 69.78; H, 6.84; N, 14.64%.

EXAMPLE 42

N-[2-Amino-2-methyl propionamido]-4-phenyl-4-[3,5(bistrifluoromethyl)benzyloxymethyl]piperidine hydrochloride Prepared from the compound of Example 2 by the method of Example 9; m.p. 156°–159° C. $C_{25}H_{28}N_2O_2F_6 \cdot HCl$ requires C, 55.71; H, 5.42; N, 5.19; Found C, 55.43; H, 5.40; N, 5.00%.

EXAMPLE 43

4 -Phenyl-4-[3,5(bistrifluoromethyl)benzyloxyethyl]piperidine hydrochloride a) 4-Acetyl-1-$^t$butyloxycarbonyl-4-phenyl piperidine 4-Acetyl-4-phenyl piperidine (2.2 g) and di-tert-butyldicarbonate (2.83 g) were dissolved in dichloromethane and stirred for one hour. The solvent was removed and the residue was recrystallised from petrol to yield a white solid (2.6 g). m/z (CI$^+$), 303.

b) 1-$^t$Butyloxycarbonyl-4-(1-hydroxyethyl)-4-phenyl piperidine,

The ketone above (2.0 g) was dissolved in methanol (20 ml) and reacted with sodium borohydride (500 mg). The reaction was stirred for one hour and the solvent was removed. The residue was purified by silica chromatography to yield a white solid (1.8 g). m/z (CI$^+$), 306 (M+1)$^+$.

c) 4-Phenyl-4-[3,5(bistrifluoromethyl)benzyloxyethyl]piperidine hydrochloride

Prepared from the compound of part b) as described in Example 2; m.p. 209°–211° C. $C_{22}H_{23}NOF_6$. HCl requires C, 56.47; H, 5.17; N, 2.99; Found C, 56.64; H, 5.27; N, 2.91%.

EXAMPLE 44

4-(3,4-Dichlorophenyl)-4-[3,5-bis(trifluoromethyl)benzyloxymethyl]piperidine hydrochloride Prepared from 3,4-dichlorophenyl acetic acid by the method of Example 14; m.p. 174° C. $C_{21}H_{19}Cl_2F_6NO$. HCl requires C, 48.25; H, 3.86; N, 2.68. Found C, 48.32; H, 3.80; N, 2.46.

EXAMPLE 45

1-[4-(3,5-Bistrifluoromethylbenzyloxymethyl)-4-phenyl-piperidin-1-yl]-2-pyridin-3-yl ethanone Prepared from the compound of Example 2 by the method of Example 9; m.p. 155° C. $C_{28}H_{26}F_6N_2O_2$. $C_7H_8SO_3$ requires C, 59.31; H, 4.84; N, 3.95. Found C, 59.30; H, 4.71; N, 3.82.

EXAMPLE 46

1-[4-(3,5-Bistrifluoromethylbenzyloxymethyl)-4-phenyl-piperidin-1-yl]-2-pyridin-2-yl ethanone tosylate Prepared from the compound of Example 2 by the method 25 of Example 9; m.p. 153° C. $C_{28}H_{26}F_6N_2O_2$. $C_7H_8SO_3$. $H_2O$ requires C, 57.85; H, 4.99; N, 3.85. Found C, 58.08; H, 4.85; N, 3.66.

EXAMPLE 47

1-[4-(3,5-Bistrifluoromethylbenzyloxymethyl)-4-phenyl-piperidin-1-yl]-2-pyridin-4-yl ethanone Prepared from the compound of Example 2 by the method of Example 9; m.p. 153° C. $C_{28}H_{26}F_6N_2O_2$. $C_7H_8SO_3$. 0.25$H_2O$ requires C, 58.94; H, 4.88; N, 3.93. Found C, 58.80; H, 4.83; N, 3.85.

EXAMPLE 48

1-[4-(3,5-Bistrifluoromethylbenzyloxymethyl)-4-phenyl-piperidin-1-yl]-3-dimethylamino-propan-1-one Prepared from the compound of Example 2 by the method of Example 9; m.p. 133° C. $C_{26}H_{30}F_6N_2O_2$. $C_7H_8SO_3$ requires C, 57.55; H, 5.56; N, 4.07. Found C, 57.81; H, 5.81; N, 3.98.

EXAMPLE 49

2-[4-(3,5-Bistrifluoromethylbenzyoxymethyl)-4-phenyl-piperidin-1-yl]acetate sodium salt Prepared from the compound of Example 2 by the method of Example 27; m.p. 183-185° C. $C_{23}H_{23}F_6NO_3$. Na requires C, 55.42; H, 4.65; N, 2.81. Found C, 55.14; H, 4.56; N, 2.80.

EXAMPLE 50

4-[4-(3,5-Bistrifluoromethylbenzyloxymethyl)-4-phenyl-piperidin-1-yl]-butyrate sodium salt Prepared from the compound of Example 2 by the method of Example 27; m.p. >230° C. $C_{25}H_{26}F_6NO_3Na$. 0.5$H_2O$ requires C, 56.18; H, 5.09; N, 2.62. Found C, 55.96; H, 5.41; N, 2.49.

EXAMPLE 51

Methyl-4-[4-(3,5-bistrifluoromethylbenzyloxymethyl)-4-phenyl-piperidin-1-yl]-butyrate hydrochloride Prepared from the compound of Example 2 by the method of Example 27; m.p. 103° C. $C_{26}H_{29}F_6NO_3$. HCl requires C, 56.37; H, 5.46; N, 2.53. Found C, 56.13; H, 5.33; N, 2.54.

EXAMPLE 52

1-[4-(3,5-Bistrifluoromethylbenzyloxymethyl)-4-phenyl-piperidin-1-yl]-3-dimethylamino ethanone tosylate Prepared from the compound of Example 2 by the method of Example 27; m.p. 186°–188° C. $C_{25}H_{28}F_6N_2O_2$. $C_7H_8SO_3$ requires C, 56.97; H, 5.38; N, 4.15. Found C, 56.89; H, 5.45; N, 4.04.

EXAMPLE 53

1-[4-(3,5-Bistrifluoromethylbenzyloxymethyl)-4-phenyl-piperidin-1-yl]-3-dimethylamino-pent-1-one tosylate Prepared from the compound of Example 2 by the method of Example 27; m.p. 130°–131° C. $C_{27}H_{32}F_6N_2O_2$. $C_7H_8SO_3H0.5H_2O$ requires C, 57.38; H, 5.81; N, 3.94. Found C, 57.26; H, 5.77; N, 4.17.

EXAMPLE 54

4-(3,5-Bistrifluoromethybenzyloxymethyl)-1-[1-(4-toluensulphonyl)-imidazole-2-yl]-methyl-4-phenyl piperidine Prepared from the compound of Example 2 by the method of Example 18; m.p. 99°–100° C. $C_{32}H_{31}F_6N_3O_3S$ requires C, 58.98; H, 4.80; N, 6.45. Found C, 59.28; H, 4.85; N, 6.32.

EXAMPLE 55

4-(3,5-Bistrifluoromethylbenzyloxymethyl)-1-(1H-imidazole-2-yl-methyl)-4-phenyl piperidine hydrochloride Prepared from the compound of Example 2 by the method of Example 18; m.p. 171° C. m/z (CI$^+$) 498.

EXAMPLE56

5-[4-(1-[3-Bromophenyl]-ethoxymethyl)-4-phenyl-piperidin-1-ylmethyl]-2,4-dihydro-[1,2,4]-triazol-3-one Prepared by the methods of Example 18 Method A and Example 12. m/z (CI$^+$) 452 (M+1)$^+$.

EXAMPLE 57

4-phenyl-4-(1-(3-Bromophenyl)-ethoxymethyl)-piperidine Hydrochloride

Prepared by the method of Example 18 Method A. m/z (CI$^+$) 375 (M+1)$^+$.

EXAMPLE 58

5-[4-(1-[3-Chlorophenyl]-ethoxymethyl)-4-phenyl-piperidin-1ylmethyl]-2,4-dihydro-[1,2,4]-triazol-3-one Prepared by the method of Example 18 Method A. m/z (CI$^+$) 392 (M+1)$^+$.

EXAMPLE 59

4-phenyl-4-[3-Iodobenzyloxymethyl]-piperidine

Prepared by the method of Examples 1 and 2. m/z (CI$^+$) 408 (M+1)$^+$.

EXAMPLE 60

5-[4-(3-Iodobenzyloxymethyl)-4-phenyl-piperidin-1-ylmethyl]-2,4-dihydro-[1,2,4]-triazol-3-one Prepared by the method of Examples 1, 2 and 12. m/z (CI$^+$) 505 (M+1)$^+$.

EXAMPLE 61

4-phenyl-4-[3-Chlorobenzyloxymethyl]-piperidine Hydrochloride

Prepared by the method of Examples 1 and 2. $C_{19}H_{22}$NOCl.HCl requires C, 64.78; H, 6.58;, 3.98. Found C, 64.85; H, 6.62; N, 3.99%.

EXAMPLE 62

5-[4-(3-Chlorobenzyloxymethyl)-4-phenyl-piperidin-1-ylmethyl]-2,4-dihydro-[1,2,4]-triazol-3-one Prepared by the method of Examples 1, 2 and 12. $C_{22}H_{25}N_4O_2Cl$ requires C, 64.00; H, 6.10; N, 13,57; Found C, 63.77; H, 5.94; N, 13.32%.

EXAMPLE 63

1-[4-(3,5-Dimethoxybenzyloxymethyl)-4-phenyl-piperidin-1yl]-2-(1H-indole-3-yl) Acetamide Prepared by the method of Examples 1, 2 and 10. m/z (CI$^+$) 499 (M+1)$^+$.

EXAMPLE 64

4-[4-(3,5-Dimethoxybenzyloxymethyl)-4-phenyl-piperidin-1ylmethyl]-Quinoline

Prepared by the method of Examples 1, 2 and 19. m/z (CI$^+$) 483 (M+1)$^+$.

EXAMPLE 65

3-[2-[4-(3,5-Dimethoxybenzyloxymethyl)-4-phenyl-piperidin-1-yl]ethyl]-1H-indole

Prepared by the method of Examples 1, 2 and 10. m/z (CI$^+$) 513 (M+1)$^+$.

EXAMPLE 66

1-(4-[3,5-Dichlorophenyl]-ethoxmethyl)-4-phenyl-piperidin-1-yl)-2-pyrrolidin-acetamide Hydrochloride Prepared by the method of Example 18 Method A and Example 10. $C_{26}H_{32}N_2O_2Cl_2$. HCl ½$H_2O$ requires C, 59.95; H, 6.56; N, 5.38; Found C, 59.76; H, 6.68; N, 5.46%.

EXAMPLE 67

4-phenyl-4-[3-$^t$-Butylbenzyloxymethyl]-piperidine.

Prepared by the method of Examples 1 and 2. m/z (CI$^+$) 338 (M+1)$^+$.

EXAMPLE 68

4-phenyl-4-[3-Cyanobenzyloxymethyl]-piperidine.

Prepared by the method of Examples 1 and 2. m/z (CI$^+$) 307 (M+1)$^+$.

EXAMPLE 69

5-[4-(3-Cyanobenzyloxymethyl)-4-phenyl-piperidin-1-ylmethyl]-2,4-dihydro-[1,2,4]-triazol-3-one Prepared by the method of Examples 1, 2 and 12. m/z (CI$^+$) 404 (M +1)$^+$.

EXAMPLE 70

4-phenyl-4-[4-Cyanobenzyloxymethyl]-piperidine Hydrochloride

Prepared by the method of Example 1 and 2. m/z (CI$^+$) 343 (M+1)$^+$.

EXAMPLE 71

5-[4-(4-Cyanobenzyloxymethyl)-4-phenyl-piperidin-1-ylmethyl]-2,4-dihydro-[1,2,4]-triazol-3-one Prepared by the method of Examples 1, 2 and 12. m/z (CI$^+$) 404 (M +1)$^+$.

EXAMPLE 72

5-[4-(3-tButylbenzyloxymethyl)-4-phenyl-piperidin-1-ylmethyl]-2,4-dihydro-[1,2,4]-triazol-3-one Prepared by the method of Examples 1, 2 and 12. m/z (CI$^+$) 435 (M+1)$^+$.

EXAMPLE 73

1-[4-(3,5-Dimethoxybenzyloxymethyl)-4-phenyl-piperidin-1-yl]-3-piperidin-4-yl-propionamide Hydrochloride Prepared by the method of Examples 1, 2 and 10. m/z (CI$^+$) 481 (M+1)$^+$.

EXAMPLE 74

1-(4-[3,5-Dichlorobenzyloxymethyl]-4-phenyl-piperidin-1-yl]-2-pyrrolidine acetamide Hydrochloride Prepared by the method of Examples 1, 2 and 10. $C_{25}H_{30}N_2O_2Cl_2$.HCl.¼$H_2O$ requires C, 59.77; H, 6.32; N, 5.37; Found C, 59.67; H, 6.42; N, 5.21%.

EXAMPLE 75

4-[3-Chloro-5-methoxybenzyloxymethyl]-4-phenyl-piperidine Hydrochloride

Prepared by the method of Examples 1 and 2. mp 150°–152° C.

EXAMPLE 76

5-[4-(3-Chloro-5-methoxybenzyloxymethyl)-4-phenyl-piperidin-1-ylmethyl]-2,4-dihydro-[1,2,4 ]-triazol-3-one Prepared by the method of Examples 1,2 and 12. mp 147°–149° C.

EXAMPLE 77

4-[3,5-Bis(trifluoromethyl)benzyloxymethyl]-4-phenyl-1-(5-pyrollidineethyl)carbamate piperidine hydrochloride a) 4-[3.5-Bis(trifluoromethyl)benzyloxymethyl]-1-(4-nitrophenyl)carbamade-4-phenylpiperidine Triethylamine (2.2 g) was added to a solution of 4-[3,5bis(trifluoromethyl)benzyloxymethyl]-4-phenylpiperidine hydrochloride (5 g) in dry dichloromethane, 85 ml and stirred for 15 mins before 4-nitrophenylcarbamate (2.2 g) was added. After 3 hrs the mixture was washed with water (×3), dried (MgSO$_4$), filtered and concentrated in vacuo. The residue was purified by flash column chromatography on silica gel eluting with 4:1 hexanes:ethyl acetate to give the title compound as a clear oil. MS CI$^+$ (559, M$^+$).

b) 4-[3,5-Bis(trifluoromethyl)benzyloxymethyl]-4-phenyl-1-(5-pyrollidine ethyl)carbamate piperidine hydrochloride The compound of part (a) (2.8 g) and 1-(2-hydroxyethyl)pyrollidine (.55 g) were dissolved in dry tetrahydrofuran (15 ml). Sodium hydride (210 mg) was added. After stirring for two hours the solvent was removed in vacuo and the residue partitioned between ethyl acetate and water. The organic layer was dried (MgSO$_4$), filtered and concentrated in vacuo. Azeotroped with toluene (×3). The residue was treated with ethereal HCl then triturated with diethyl ether to give the title compound. NMR (360 MHz, DMSO) 1.81–1.93 (6H, m), 2.14–2.19 (2H, m), 3.05 (4H, broad), 3.40 (2H, s), 3.72 (2H, broad), 3,52 (4H, s), 4.33 (2H, s), 4.55 (2H, s), 7.22–7.44 (5H, m), 7.74 (2H,s), 7.94 (1H, s), 11.23 (broad, N$^+$H$_2$).

EXAMPLE 78

5-[4-(3,5-Bismethylbenzyloxymethyl)-4-phenyl-piperdin-1-ylmethyl]-2,4,dihydro-[1,2,4 ]-triazol-3-one
Prepared as described in Examples 1, 2 and 12. mp 144°–145° C.

EXAMPLE 79

(±)-5-[4-(1-(3-N,N-Dimethylphenyl)-ethoxymethyl)-4-phenyl-piperidin-1-ylmethyl]-2,4-dihydro-[1,2,4]-triazol-3-one
Prepared as described in Example 18 Method B and Example 12. m/z (CI)$^+$ 435 (M+1)$^+$.

EXAMPLE 80

4-Phenyl-4-[1-(3-Isoproxy)benzyloxymethyl]piperidine Hydrochloride
Prepared as described in Examples 1, 2 and Example 12. m/z (CI)$^+$ 354 (M+1)$^+$.

EXAMPLE 81

5-[4-(1-(3-Isopropoxyphenyl)-ethoxmethyl)-4-piperidin, 1-ylmethyl-2,4-dihydro-[1,2,41 triazol-3-one
Prepared as described in Example 18 Method A and Example 12. m/z (CI)$^+$ 451 (M+1)$^+$.

EXAMPLE 82

4-Phenyl-4-(2-cyanobenzyloxymethyl)piperidine Hydrochloride
Prepared as described in Examples 1 and 2. m/z (CI)$^+$ 307 (M+1)$^+$.

EXAMPLE 83

4-(4-Methoxyphenyl)-4-[(3,5-bistrifluoromethyl)benzyloxymethyl]piperidine Hydrochloride
Prepared as described in Example 14. m/z (CI)$^+$ 448 (M+1)$^+$.

EXAMPLE 84

4-Phenyl-4-[(2-methoxy-5-bromo)benzyloxymethyl]piperidine Hydrochloride
Prepared as described in Examples 1 and 2. m/z (CI)$^+$ 390 (M+1)$^+$.

EXAMPLE 85

4-Phenyl-4-[1-(3,6-dichlorophenyl)-ethoxymethyl]piperidine Hydrochloride
Prepared as described in Example 18 Method A and Example 12. mp 120°–128° C. m/z (CI)$^+$ 364 (M+1)$^+$.

EXAMPLE 86

4-Phenyl-4-[1-(2,3-dichlorophenyl)-ethoxymethyl]piperidine Hydrochloride
Prepared as described in Example 18 Method A and Example 12. m/z (CI)$^+$ 364 (M+1)$^+$.

EXAMPLE 87

4-Phenyl-4-[2,3-(dimethoxy)benzyloxymethyl]piperidine Hydrochloride
Prepared as described in Example 18 Method A and Example 12. m/z (CI)$^+$ 439 (M+1)$^+$.

EXAMPLE 88

5-[4-(3-Isopropoxy)benzyloxymethyl-4-phenyl-piperidin-1-ylmethyl]-2,4-dihydro-[1,2,4]-triazol-3-one
mp 140° C.

EXAMPLE 89

4-[3-(Trifluoromethoxy)benzyloxymethyl]-4-phenyl-piperidine Hydrochloride
mp 129° C.

EXAMPLE 90

The compound of Example 56 (15 mg) was resolved by HPLC (CHIRACEL OJ. 5% EtOH/hexane 40° C.) to afford the single enantiomers:
(+)5-[4-(1-[3-Bromophenyl]-ethoxymethyl)-4-phenyl-piperidin-1-ylmethyl]-2,4-dihydro-[1,2,4]-triazol-3-one. [α]$^{23}_D$=23.8° (6.0 mg).
(−)5-[4-(1-[3-Bromophenyl]-ethoxymethyl)-4-phenyl-1-ylmethyl]-2,4-dihydro-[1,2,4]-triazol-3-one. [α]$^{23}_D$= 24.2° (8.2 mg).

We claim:
1. A compound of formula (I)

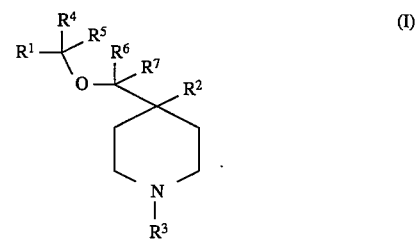

wherein:

R$^1$ represents phenyl substituted by 1, 2 or 3 groups selected from C$_{1-6}$alkyl, C$_{2-6}$alkenyl, C$_{2-6}$alkynyl, halo, cyano, nitro, trifluoromethyl, trimethylsilyl,— OR$^a$, SR$^a$, SOR$^a$, SO$_2$R$^a$, —NR$^a$R$^b$, —NR$^a$COR$^b$, —NR$^a$CO$_2$R$^b$, —CO$_2$R$^a$ or —CONR$^a$R$^b$, where R$^a$ and R$^b$ each independently represent H, C$_{1-6}$alkyl, phenyl or trifluoromethyl;

R$^2$ represents phenyl optionally substituted by 1, 2 or 3 groups selected from C$_{1-6}$alkyl, C$_{2-6}$alkenyl, C$_{2-6}$alkynyl, halo, cyano, nitro, trifluoromethyl, trimethylsilyl, —OR$^a$, SR$^a$, SOR$^a$, SO$_2$R$^a$, —NR$^a$R$^b$, —NR$^a$COR$^b$, —NR$^a$CO$_2$R$^b$, —CO$_2$R$^a$ or —CONR$^a$R$^b$; heteroaryl selected from indazolyl, thienyl, furyl, pyridyl, thiazolyl, tetrazolyl and quinolyl; benzhydryl; or benzyl; wherein each heteroaryl and each phenyl moiety of benzyl and benzhydryl may be substituted by C$_{1-6}$alkyl, C$_{1-6}$alkoxy, halo or trifluoromethyl;

R³ represents H, COR⁹, CO₂R¹⁰, COCONR¹⁰R¹¹, COCO₂R¹⁰, SO₂R¹⁵, CONR¹⁰SO₂R¹⁵, $C_{1-6}$alkyl optionally substituted by a group selected from (CO₂R¹⁰, CONR¹⁰R¹¹, hydroxy, cyano, COR⁹, NR¹⁰R¹¹, C(NOH)NR¹⁰R¹¹, CONHphenyl($C_{1-4}$alkyl), COCO₂R¹⁰, COCONR¹⁰R¹¹, SO₂R¹⁵, CONR¹⁰SO₂R¹⁵ and phenyl optionally substituted by one or more substituents selected from $C_{1-6}$alkyl, $C_{1-6}$alkoxy, halo and trifluoromethyl), Y—R⁸ or CO-Z-(CH₂)₁—R¹²;

R⁴, R⁵, R⁶ and R⁷ each independently represent H or $C_{1-6}$alkyl;

R⁸ represents an aromatic heterocyclic group selected from thienyl, furyl, pyrrolyl, pyridyl, pyrazolyl, triazolyl, tetrazolyl, thiazolyl, pyrazinyl, pyrimidinyl, pyridazinyl, triazinyl, oxazolyl, oxadiazolyl, thiadiazolyl, isoxazolyl, quinolyl, isothiazolyl, imidazolyl, benzimidazolyl, benzoxazolyl, benzothiophenyl, benzofuranyl and indolyl, any of which may be substituted by one or more groups selected from $C_{1-6}$alkyl, $C_{1-6}$alkoxy, phenyl, oxo, thioxo, halo, trifluoromethyl, NRᵃRᵇ, NRᵃCORᵇ, CONRᵃRᵇ, CO₂Rᵃ, SRᵃ, SO₂Rᵃ and CH₂ORᵃ;

R⁹ represents H, $C_{1-6}$alkyl or phenyl;

R¹⁰ and R¹¹ each independently represent H or $C_{1-6}$alkyl;

R¹² represents NR¹³R¹⁴ or an optionally substituted aromatic or non-aromatic azacyclic or azabicyclic group optionally containing in the ring one or more heteroatoms selected from O, S and N, or the group NR¹⁶, and may be unsubstituted or substituted by a group selected from $C_{1-6}$alkyl, $C_{1-6}$alkoxy, oxo, SH, =S, halo, trifluoromethyl, NRᵃRᵇ, NRᵃCORᵇ, CONRᵃRᵇ, CO₂Rᵃ and CH₂ORᵃ;

R¹³ and R¹⁴ each independently represent H, $C_{1-6}$alkyl, phenyl optionally substituted by one or more of $C_{1-6}$alkyl, $C_{1-6}$alkoxy, halo or trifluoromethyl or phenyl$C_{1-4}$alkyl optionally substituted in the phenyl ring by one or more of $C_{1-6}$alkyl, $C_{1-6}$alkoxy, halo or trifluoromethyl;

R¹⁵ represents $C_{1-6}$alkyl, trifluoromethyl or phenyl optionally substituted by one or more substituents selected from $C_{1-6}$alkyl, $C_{1-6}$alkoxy, halo and trifluoromethyl;

R¹⁶ represents H, $C_{1-6}$alkyl or phenyl$C_{1-4}$alkyl;

Y represents a hydrocarbon chain of 1,2,3 or 4 carbon atoms which may optionally be substituted by oxo;

Z represents CH₂, O, S or NR¹⁰; and q represents 0, 1, 2, 3, 4, 5 or 6;

or a pharmaceutically acceptable salt thereof.

2. The compound of claim 1 wherein:

R² is phenyl or substituted phenyl, or a pharmaceutically acceptable salt thereof.

3. The compound of claim 1 wherein R⁴, R⁶ and R⁷ are H.

4. The compound of claim 28 wherein R⁵ is methyl.

5. The compound of claim 1 wherein R¹ is phenyl substituted in either or both of the 3-and/or the 5-positions by a group selected from: chloro, bromo, methyl, t-butyl, trifluoromethyl, methoxy, ethoxy, n-propyl, isopropyl, n-butyl, sec-butyl, or t-butyl.

6. The compound of claim 1 wherein R³ is H.

7. The compound of claim 1 wherein R³ is Y—R⁸ wherein Y is as defined in claim 1 and R⁸ is a group selected from: oxazolyl, oxadiazolyl, imidazolyl, thiadiazolyl, triazolyl, pyrazinyl, pyridazinyl, or triazinyl, wherein the group is optionally substituted by a substituent selected from: methyl, methoxy, phenyl, oxo, thioxo, bromo, iodo, —NH₂, —SCH₃, —COOH, or cyano.

8. The compound of claim 1 wherein R⁶ and R⁷ together with the carbon atom to which they are attached represent a C=C(R⁴¹)(R⁵¹) group wherein R⁴¹ and R⁵¹ are independently hydrogen or $C_{1-5}$alkyl.

9. The compound of claim 1 which is selected from the group consisting of:

4-phenyl-4-[(3,5-bistrifluoromethyl)benzyloxymethyl]piperidine;

4-phenyl-4-[(2-trifluoromethyl)benzyloxymethyl]piperidine;

4-phenyl-4-benzyloxymethylpiperidine;

4-phenyl-4-[(3-chloro-5-t-butyl)benzyloxymethyl]piperidine;

4-phenyl-4-[(3,5-dichloro)benzyloxymethyl]piperidine;

4-phenyl-4-[(3-trifluoromethyl)benzyloxymethyl]piperidine;

4-phenyl-4-[(4-trifluoromethyl)benzyloxymethyl]piperidine;

1-acetyl-4-phenyl-4-[(3,5-bistrifluoromethyl)benzyloxymethyl]piperidine;

1-methanesulphonyl-4-phenyl-4-[(3,5-bistrifluoromethyl) benzyloxymethyl]piperidine;

5-[(4-[(3,5-bistrifluoromethyl)benzyloxymethyl ]-4-phenylopiperidin-1-ylmethyl]-2,4-dihydro[1,2,4]triazol-3-one;

2-[1'-imidazolyl]acetyl-4-phenyl-4-[(3,5-bistrifluoromethyl) benzyloxymethyl]piperidine;

5-[4-[(3,5-bistrifluoromethyl)benzyloxymethyl]-4-(4-fluorophenyl)-piperidin-1-ylmethyl]-2,4-dihydro[1,2,4]triazol-3-one;

5-[4-[(3,5-bistrifluoromethyl)benzyloxymethyl]-4-(2-fluorophenyl)-piperidin-1-yl)methyl]-2,4-dihydro[1,2,4]triazol-3-one;

5-[4-[(3,5-bistrifluoromethyl)benzyloxymethyl]-4-(3-fluorophenyl)-piperidin-1-yl)methyl]-2,4-dihydro[1,2,4]triazolo-3-one;

3-phenyl-3-[(3,5-bistrifluoromethyl)benzyloxymethyl]piperidine);

4-phenyl-[4-[1-(3,5-bis(trifluoromethyl)phenyl]ethoxymethyl]piperidine;

1-methyl-4-phenyl-4-[3,5-bis(trifluoromethyl)benzyloxymethyl]piperidine;

1-isopropyl-4-phenyl-4-[3,5-bis(trifluoromethyl)benzyloxymethyl]piperidine;

1-(2-phenyl)ethyl-4-phenyl-4-[3,5-bis(trifluoromethyl)benzyloxymethyl]piperidine;

1-isobutyryl-4-phenyl-4-[3,5-bis(trifluoromethyl)benzyloxymethyl]piperidine;

1-isovaleryl-4-phenyl-4-[3,5-bis(trifluoromethyl)benzyloxymethyl]piperidine;

(±)-5-[4-[1-(3,5-bis(trifluoromethyl)phenyl]ethoxymethyl]-4-phenyl-piperidin-1-yl]-2,4-dihydro-[1,2,4]triazol-3-one;

4-phenyl-4-[(3-chloro-5-methyl)benzyloxymethyl]piperidine;

4-phenyl-4-[(3-bromo-5-methyl)benzyloxymethyl]piperidine;

4-phenyl-4-[(3-methyl-5-t-butyl)benzyloxymethyl]piperidine;

methyl-2-[4-phenyl-4-(3,5-bis(trifluoromethyl)benzyloxymethyl) piperidine]acetate;

N-methyl-4-phenyl-4-[3,5-bis(trifluoromethyl)benzyloxymethyl]piperidine;

4-[3,5-bis(trifluoromethyl)benzyloxymethyl]-4-phenyl-1-(4H-[1,2,4]triazol-3-yl-methyl)piperidine;

5-[4-(3-methyl-5-t-butyl)benzyloxymethyl)4-phenylpiperidin-1-ylmethyl]2,4-dihydro-[1,2,4 ]triazol-3-one;

2-[4-phenyl-4-[3,5-bis(trifluoromethyl)benzyloxymethyl]-N-3-pyridylmethyl-N-methylacetamide;

4-[3,5-bis(trifluoromethyl)benzyloxymethyl]-1-(2-methylthiazol-5-ylmethyl)-4-phenylpiperidine;

4-[3,5-bis(trifluoromethyl)benzyloxymethyl]-1-[1,2,4]oxadiazol-3-ylmethyl-4-phenylpiperidine;

(±)-5-[4-(3,5-bis(trifluoromethyl)benzyloxymethyl)-4-phenylpiperidinyl-1-ethyl]-2,4-dihydro-[1,2,4]triazol-3-one;

1-[4-(3,5-bis(trifluoromethyl)benzyloxymethyl-4-phenylpiperidin-1-yl)-2-pyrrolidin-1-ylacetamide;

N-methanesulphonyl-2-[4-phenyl-4-(3,5-bis(trifluoromethyl) benzyloxymethyl)piperidin-1-yl]acetamide;

N-phenylsulphonyl-2-[4-phenyl-4-(3,5-bis(trifluoromethyl)benzyloxymethyl) piperidin-1-yl]acetamide;

4-phenyl-4-[(3-phenyl)benzyloxymethyl]piperidine;

5-[4-(3-phenyl)benzyloxymethyl]-4-phenylpiperidin-1-ylmethyl-2,4-dihydro-[1,2,4]triazol-3-one;

5-[(4-benzyloxymethyl)-4-phenyl-piperidin-1-ylmethyl]-2,4-dihydro-[1,2,4]triazol-3-one;

N-[2-amino-2-methylpropionamido]-4-phenyl-4-[3,5-bis(trifluoromethyl) benzyloxymethyl]piperidine;

4-phenyl-4-[3,5-bis(trifluoromethyl)benzyloxyethyl]piperidine;

4(3,4-dichlorophenyl)-4-[3,5-bis(trifluoromethyl)benzyloxymethyl]piperidine;

1-[4-(3,5-bis(trifluoromethyl)benzyloxymethyl)-4-phenyl-piperidin-1-yl]-2-pyridin-3-ylethanone;

1-[4-(3,5-bis(trifluoromethyl)benzyloxymethyl)-4-phenyl-piperidin-1-yl ]-2-pyridin-2-ylethanone;

1-[4-(3,5-bis(trifluoromethyl)benzyloxymethyl)-4-phenyl-piperidin-1-yl]-2-pyridin-4-ylethanone;

1-[4-(3,5-bis(trifluoromethyl)benzyloxymethyl)-4-phenyl-piperidin-1-yl]-3-dimethylamino-propan-1-one;

2-[4-(3,5-bis(trifluoromethyl)benzyloxymethyl)-4-phenyl-piperidin-1-yl]acetate;

4-[4-(3,5-bis(trifluoromethyl)benzyloxymethyl)-4-phenyl-piperidin-1-yl]butyrate;

methyl-4-[4-(3,5-bis(trifluoromethyl)benzyloxymethyl)-4-phenyl-piperidin-1-yl]butyrate;

1-[4-(3,5-bis(trifluoromethyl)benzyloxymethyl)-4-phenyl-piperidin-1-yl]-3-dimethylaminoethanone;

1-[4-(3,5-bis(trifluoromethyl)benzyloxymethyl)-4-phenyl-piperidin-1-yl]-3-dimethylaminopent-1-one;

4-(3,5-bis(trifluoromethyl)benzyloxymethyl)-1-[1-(4-toluenesulphonyl)-imidazole-2-yl]methyl-4-phenylpiperidine;

4-(3,5-bis(trifluoromethyl)benzyloxymethyl)-1-(1H-imidazole-2-yl-methyl)-4-phenylpiperidine;

5-[4-(1-[3-bromophenyl]-ethoxymethyl)-4-phenyl-piperidin-1-ylmethyl]-2,4-dihydro-[1,2,4 ]-triazol-3-one;

4-phenyl-4-(1-(3-bromophenyl)-ethoxymethyl)-piperidine hydrochloride;

5-[4-(1-[3-chlorophenyl]-ethoxymethyl)-4-phenyl-piperidin-1-ylmethyl]-2,4-dihydro-[1,2,4]-triazol-3-one;

4-phenyl-4-[3-iodobenzyloxymethyl]-ethoxymethyl)-piperidine;

5-[4-(3-iodobenzyloxymethyl)-4-phenyl-piperidin-1-ylmethyl]-2,4-dihydro-[1,2,4]-triazol-3-one;

4-phenyl-4-[3-chlorobenzyloxymethyl]-piperidine hydrochloride;

5-[4-(3-chlorobenzyloxymethyl)-4-phenyl-piperidin-1-ylmethyl]-2,4-dihydro-[1,2,4]-triazol-3-one;

1-[4-(3,5-dimethoxybenzyloxymethyl)-4-phenyl-piperidin-1-yl]-2-(1H-indole-3-yl)acetamide;

4-[4-(3,5-dimethoxybenzyloxymethyl)-4-phenyl-piperidin-1-ylmethyl]quinoline;

3-[2-[4-(3,5-dimethoxybenzyloxymethyl)-4-phenyl-piperidin-1-yl]ethyl]-1H-indole;

1-(4-[3,5-dichlorophenyl]-ethoxymethyl)-4-phenyl-piperidin-1-yl)-2-pyrrolidin-acetamide hydrochloride;

4-phenyl-4-[3-t-butylbenzyloxymethyl]-piperidine;

4-phenyl-4-[3-cyanobenzyloxymethyl]-piperidine;

5-[4-(3-cyanobenzyloxymethyl)-4-phenyl-piperidin-1-ylmethyl]-2,4-dihydro-[1,2,4]-triazol-3-one;

4-phenyl-4-[4-cyanobenzyloxymethyl]-piperidine hydrochloride;

5-[4-(4-cyanobenzyloxymethyl)-4-phenyl-piperidin-1-ylmethyl]-2,4-dihydro-[1,2,4]-triazol-3-one;

5-[4-(3-t-butylbenzyloxymethyl)-4-phenyl-piperidin-1-ylmethyl]-2,4-dihydro-[1,2,4]-triazol-3-one;

1-[4-(3,5-dimethoxybenzyloxymethyl)-4-phenyl-piperidin-1-yl]-3-piperidin-4-yl-propionamide hydrochloride;

1-(4-(3,5-dichlorobenzyloxymethyl)-4-phenyl-piperidin-1-yl]-2-pyrrolidine acetamide hydrochloride;

4-[3-chloro-5-methoxybenzyloxymethyl)-4-phenyl-piperidine hydrochloride;

5-[4-(3-chloro-5-methoxybenzyloxymethyl)-4-phenyl-piperidin-1-ylmethyl]-2,4-dihydro-[1,2,4]-triazol-3-one;

4-[3,5-bis(trifluoromethyl)benzyloxymethyl]-4-phenyl-1-(5-pyrrollodineethyl)carbamate piperidine hydrochloride;

5-[4-(3,5-bismethylbenzyloxymethyl)-4-phenyl-piperidin-1-ylmethyl]-2,4-dihydro-[1,2,4]-triazol-3-one;

(±)-5-[4-(1-(3-N,N-dimethylphenyl)-ethoxymethyl)-4-phenyl-piperidin-1-ylmethyl]-2,4-dihydro-[1,2,4]-triazol-3-one;

4-phenyl-4-[1-(3-isopropoxy)benzyloxymethyl]piperidine hydrochloride;

5-[4-(1-(3-isopropoxyphenyl)-ethoxymethyl)-4-phenyl-piperidin-1-ylmethyl]-2,4-dihydro-[1,2,4]-triazol-3-one;

4-phenyl-4-(2-cyanobenzyloxymethyl)piperidine hydrochloride;

4-(4-methoxyphenyl)-4-[(3,5-bis(trifluoromethyl)benzyloxymethyl]piperidine hydrochloride;

4-phenyl-4-[(2-methoxy-5-bromo)benzyloxymethyl]piperidine hydrochloride;

4-phenyl-4-[1-(3,6-dichlorophenyl)-ethoxymethyl]piperidine hydrochloride;

4-phenyl-4-[1-(2,3-dichlorophenyl)-ethoxymethyl]piperidine hydrochloride;

4-phenyl-4-[2,3-(dimethoxy)benzyloxymethyl]piperidine hydrochloride;

or a pharmaceutically acceptable salt thereof.

10. A pharmaceutical composition comprising a compound of claim 1 or a pharmaceutically acceptable salt thereof in association with a pharmaceutical carrier therefor.

11. A method for the treatment or prevention of physiological disorders associated with an excess of tachykinins which comprises administering to a patient in need thereof a tachykinin reducing amount of a compound of claim 1 or a pharmaceutically acceptable salt thereof.

12. A process for the preparation of a compound as claimed in claim 1 which comprises reacting a compound of formula (II) with a compound of formula (III):

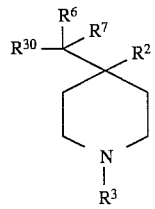
(II)

(III)

wherein $R^1$, $R^2$, $R^4$, $R^5$, $R^6$, and $R^7$ are as defined in claim 1, $R^3$ is as defined in claim 1 except that, when $R^3$ is H it is replaced by a suitable protecting group; and one of $R^{30}$ and $R^{31}$ represents a leaving group and the other of $R^{30}$ and $R^{31}$ represents XH, where X is as defined in claim 1; in the presence of a base, followed by deprotection, if required.

* * * * *